United States Patent
Zurn

(10) Patent No.: US 9,962,533 B2
(45) Date of Patent: May 8, 2018

(54) MODULE FOR TREATMENT OF MEDICAL CONDITIONS; SYSTEM FOR MAKING MODULE AND METHODS OF MAKING MODULE

(71) Applicant: William Harrison Zurn, Sunnyvale, CA (US)

(72) Inventor: William Harrison Zurn, Sunnyvale, CA (US)

(*) Notice: Subject to any disclaimer, the term of this patent is extended or adjusted under 35 U.S.C. 154(b) by 0 days. days.

(21) Appl. No.: 13/767,671

(22) Filed: Feb. 14, 2013

(65) Prior Publication Data

US 2014/0228819 A1 Aug. 14, 2014

(51) Int. Cl.
*A61M 37/00* (2006.01)
*H02J 7/02* (2016.01)
*H02J 5/00* (2016.01)
*H02J 17/00* (2006.01)

(52) U.S. Cl.
CPC .............. *A61M 37/00* (2013.01); *H02J 5/005* (2013.01); *H02J 7/02* (2013.01); *H02J 7/025* (2013.01); *H02J 17/00* (2013.01)

(58) Field of Classification Search
CPC ... A61B 5/0002; A61B 5/0031; A61B 5/0093; A61B 5/02; A61B 5/0215; A61B 5/076; A61B 19/54; A61B 5/05; A61M 1/00; A61M 31/00; G05B 19/02
USPC ............ 604/500; 600/12; 606/194; 128/898; 623/1.11, 1.13
See application file for complete search history.

(56) References Cited

U.S. PATENT DOCUMENTS

| | | | |
|---|---|---|---|
| 3,657,744 A | 4/1972 | Ersek | |
| 3,976,729 A | 8/1976 | Lewis et al. | |
| 4,061,134 A | 12/1977 | Samuels et al. | |
| 4,097,736 A | 6/1978 | Jacobson et al. | |
| 4,140,126 A | 2/1979 | Choudhury | |
| 4,210,666 A | 7/1980 | Munson, Jr. | |
| 4,262,202 A | 4/1981 | Cusano et al. | |
| 4,276,874 A | 7/1981 | Wolvek et al. | |
| 4,446,548 A | 5/1984 | Bouwhuis et al. | |
| 4,467,351 A | 8/1984 | Wang | |
| 4,557,626 A | 12/1985 | McKay et al. | |
| 4,560,374 A | 12/1985 | Hammerslag | |
| 4,617,932 A | 10/1986 | Kornbeg | |
| 4,624,665 A * | 11/1986 | Nuwayser | ..................... 604/307 |
| 4,650,466 A | 3/1987 | Luther | |

(Continued)

OTHER PUBLICATIONS

"Deposition Cyclotron". Google. Accessed online May 20, 2015. <https://www.google.com/search?q=%22deposition+cyclotron%22>.*

(Continued)

*Primary Examiner* — Scott Medway
(74) *Attorney, Agent, or Firm* — Law Office of Alan W. Cannon

(57) ABSTRACT

A module producible inside a living body is provided. The module includes an instructions receiver configured to receive wireless transmissions of instructions from a master controller located outside of the body when the module is inside the body. An energy receiver configured to receive wireless transmission of non-destructive energy from the master controller located outside of the body when the module is inside the body. The module further includes a battery and a communications and guide element electrically connected to the instructions receiver, the energy receiver and the battery.

18 Claims, 12 Drawing Sheets

(56) References Cited

U.S. PATENT DOCUMENTS

| | | |
|---|---|---|
| 4,654,024 A | 3/1987 | Crittenden et al. |
| 4,655,771 A | 4/1987 | Wallsten |
| 4,672,961 A | 6/1987 | Davies |
| 4,692,147 A * | 9/1987 | Duggan .................. 604/891.1 |
| 4,718,076 A | 1/1988 | Doi et al. |
| 4,728,328 A | 3/1988 | Hughes et al. |
| 4,732,152 A | 3/1988 | Wallsten et al. |
| 4,739,762 A | 4/1988 | Palmaz |
| 4,787,899 A | 11/1988 | Lazarus |
| 4,795,458 A | 1/1989 | Regan |
| 4,799,925 A | 1/1989 | Rosenblatt |
| 4,819,632 A | 4/1989 | Davies |
| 4,830,003 A | 5/1989 | Wolff et al. |
| 4,873,708 A | 10/1989 | Cusano et al. |
| 4,892,539 A | 1/1990 | Koch |
| 4,913,141 A | 4/1990 | Hillstead |
| 4,954,126 A | 9/1990 | Wallsten |
| 4,969,896 A | 11/1990 | Shors |
| 4,994,071 A | 2/1991 | MacGregor |
| 4,995,386 A | 2/1991 | Ng |
| 4,998,539 A | 3/1991 | Delsanti et al. |
| 4,998,972 A | 3/1991 | Chi et al. |
| 5,024,671 A | 6/1991 | Tu |
| 5,026,377 A | 6/1991 | Burton et al. |
| 5,035,706 A | 7/1991 | Giantureo et al. |
| 5,047,050 A | 9/1991 | Arpesani |
| 5,078,726 A | 1/1992 | Kreamer |
| 5,084,065 A | 1/1992 | Weldon |
| 5,090,959 A | 2/1992 | Samson et al. |
| 5,096,388 A * | 3/1992 | Weinberg .................. 417/413.3 |
| 5,100,426 A | 3/1992 | Nixon |
| 5,102,417 A | 4/1992 | Palmaz |
| 5,104,399 A | 4/1992 | Lazarus |
| 5,104,404 A | 4/1992 | Wolff |
| 5,117,445 A | 5/1992 | Seppi et al. |
| 5,122,154 A | 6/1992 | Rhodes |
| 5,123,917 A | 6/1992 | Lee |
| 5,158,548 A | 10/1992 | Lau |
| 5,192,297 A | 3/1993 | Hull |
| 5,201,757 A | 4/1993 | Heyn et al. |
| 5,207,695 A | 5/1993 | Trout, III |
| 5,219,355 A | 6/1993 | Parodi et al. |
| 5,237,993 A * | 8/1993 | Skrabal .................. 600/309 |
| 5,275,622 A | 1/1994 | Lazarus et al. |
| 5,282,824 A | 2/1994 | Gianturco |
| 5,316,023 A | 5/1994 | Palmaz et al. |
| 5,333,969 A | 8/1994 | Blaha et al. |
| 5,373,833 A | 10/1994 | D'Andrade |
| 5,374,974 A | 10/1994 | Rostoker et al. |
| 5,360,443 A | 11/1994 | Barong et al. |
| 5,362,176 A | 11/1994 | Sovik et al. |
| 5,395,334 A | 3/1995 | Keith et al. |
| 5,397,345 A | 3/1995 | Lazarus |
| 5,475,729 A | 12/1995 | Mattson et al. |
| 5,489,295 A | 2/1996 | Piplani et al. |
| 5,514,873 A | 5/1996 | Schulze-Ganzlin et al. |
| 5,549,412 A | 8/1996 | Malone et al. |
| 5,562,728 A | 10/1996 | Lazarus |
| 5,609,625 A | 3/1997 | Piplani |
| 5,628,783 A | 5/1997 | Quiachon |
| 5,642,394 A | 6/1997 | Rothschild |
| 5,662,700 A | 9/1997 | Lazarus |
| 5,669,936 A | 9/1997 | Lazarus |
| 5,680,858 A * | 10/1997 | Hansen et al. .................. 600/345 |
| 5,721,685 A | 2/1998 | Holland et al. |
| 5,725,842 A | 3/1998 | Boucher, Jr. et al. |
| 5,741,246 A | 4/1998 | Prescott |
| 5,788,468 A * | 8/1998 | Dewa et al. .................. 417/415 |
| 5,824,015 A | 10/1998 | Sawyer |
| 5,830,209 A | 11/1998 | Savage et al. |
| 5,855,599 A | 1/1999 | Wan |
| 5,902,567 A | 5/1999 | Boucher, Jr. |
| 5,932,481 A | 8/1999 | Pon et al. |
| 5,951,566 A | 9/1999 | Lev |
| 5,964,223 A | 10/1999 | Baran |
| 6,004,269 A | 12/1999 | Crowley et al. |
| 6,019,784 A | 2/2000 | Hines |
| 6,022,527 A | 2/2000 | Boucher, Jr. et al. |
| 6,027,863 A | 2/2000 | Donadio, III |
| 6,033,398 A | 3/2000 | Farley et al. |
| 6,051,017 A * | 4/2000 | Loeb et al. .................. 607/1 |
| 6,074,374 A | 6/2000 | Fulton |
| 6,107,004 A | 8/2000 | Donadio, III |
| 6,116,863 A * | 9/2000 | Ahn .................. F04B 43/043 417/322 |
| 6,133,247 A | 10/2000 | Boucher, Jr. |
| 6,139,511 A | 10/2000 | Millet |
| 6,146,814 A | 11/2000 | Huter et al. |
| 6,168,579 B1 | 1/2001 | Tsugita |
| 6,203,732 B1 | 3/2001 | Clubb et al. |
| 6,210,362 B1 | 4/2001 | Ponzi |
| 6,214,536 B1 | 4/2001 | Boucher, Jr. |
| 6,241,745 B1 | 6/2001 | Rosenthal |
| 6,251,128 B1 | 6/2001 | Knopp et al. |
| 6,368,275 B1 * | 4/2002 | Sliwa et al. .................. 600/437 |
| 6,374,476 B1 | 4/2002 | Ponzi et al. |
| 6,398,792 B1 | 6/2002 | O'Connor |
| 6,441,569 B1 | 8/2002 | Janzow |
| 6,520,934 B1 | 2/2003 | Lee et al. |
| 6,524,303 B1 | 2/2003 | Garibaldi |
| 6,620,148 B1 | 3/2003 | Tsugita |
| 6,595,949 B1 | 7/2003 | Shapiro |
| 6,673,104 B2 | 1/2004 | Barry |
| 6,696,335 B2 | 2/2004 | Bonart |
| 6,786,896 B1 | 9/2004 | Madhani et al. |
| 6,926,670 B2 | 8/2005 | Rich et al. |
| 6,931,092 B2 | 8/2005 | Joshi et al. |
| 6,968,743 B2 | 11/2005 | Rich et al. |
| 6,980,843 B2 | 12/2005 | Eng et al. |
| 6,986,757 B1 | 1/2006 | Kumasaki et al. |
| 6,997,918 B2 | 2/2006 | Soltesz et al. |
| 6,998,358 B2 | 2/2006 | French et al. |
| 7,062,008 B2 | 6/2006 | Joshi et al. |
| 7,081,133 B2 * | 7/2006 | Chinn et al. .................. 623/2.41 |
| 7,137,393 B2 | 11/2006 | Pivovarov |
| 7,204,252 B2 | 4/2007 | Johnson |
| 7,242,301 B2 | 7/2007 | August et al. |
| 7,278,429 B2 | 10/2007 | Johnson |
| 7,313,221 B2 | 12/2007 | Sowerby et al. |
| 7,344,507 B2 * | 3/2008 | Briggs .................. A61B 5/150832 600/583 |
| 7,402,808 B2 | 7/2008 | Rose et al. |
| 7,403,756 B1 | 7/2008 | Jiacinto et al. |
| 7,462,419 B2 | 12/2008 | LaFollette et al. |
| 7,463,716 B2 | 12/2008 | Tseng |
| 7,463,717 B2 | 12/2008 | Tseng |
| 7,466,798 B2 | 12/2008 | Borgstahl et al. |
| 7,512,210 B2 | 3/2009 | Possin et al. |
| 7,607,440 B2 | 10/2009 | Coste-Maniere et al. |
| 7,647,831 B2 | 1/2010 | Corcoran et al. |
| 7,654,130 B2 | 2/2010 | Shah et al. |
| 7,699,059 B2 | 4/2010 | Fonseca et al. |
| 7,727,147 B1 * | 6/2010 | Osorio et al. .................. 600/365 |
| 7,777,641 B2 * | 8/2010 | Karunasiri et al. .............. 607/56 |
| 7,790,226 B2 | 9/2010 | Tai et al. |
| 7,811,279 B2 * | 10/2010 | John .................. 604/890.1 |
| 7,831,210 B1 | 11/2010 | Freeman et al. |
| 7,839,153 B2 | 11/2010 | Joy et al. |
| 7,851,456 B2 | 12/2010 | Boyer et al. |
| 7,899,578 B2 | 3/2011 | Prisco et al. |
| 7,907,166 B2 | 3/2011 | Lamprecht et al. |
| 7,916,831 B2 | 3/2011 | Sun et al. |
| 7,929,741 B2 | 4/2011 | Guiliguian et al. |
| 7,938,123 B2 | 5/2011 | Danek et al. |
| 7,945,229 B2 | 5/2011 | Wilson et al. |
| 7,961,224 B2 | 6/2011 | Cheimets |
| 7,967,754 B2 | 6/2011 | Knight |
| 7,979,108 B2 | 7/2011 | Zurn |
| 8,067,741 B2 | 11/2011 | Beekman |
| 8,167,871 B2 * | 5/2012 | Hyde et al. .................. 604/891.1 |
| 8,172,826 B2 * | 5/2012 | Hyde et al. .................. 604/500 |
| 8,180,022 B2 | 5/2012 | Tseng et al. |
| 8,204,171 B2 | 6/2012 | Ikhlef |
| 8,237,128 B2 | 8/2012 | Steadman Booker et al. |

(56) References Cited

U.S. PATENT DOCUMENTS

| | | | | |
|---|---|---|---|---|
| 8,317,737 | B2* | 11/2012 | Hyde et al. | 604/4.01 |
| 8,350,221 | B2 | 1/2013 | Steadman Booker et al. | |
| 8,663,209 | B2 | 3/2014 | Zurn | |
| 8,723,120 | B2 | 5/2014 | Atzinger et al. | |
| 8,847,168 | B2 | 9/2014 | Kim et al. | |
| 9,035,269 | B2 | 5/2015 | Torregrosa et al. | |
| 9,220,921 | B2 | 12/2015 | Chen | |
| 9,274,235 | B2 | 3/2016 | Kang et al. | |
| 9,305,784 | B2 | 4/2016 | Ninomiya et al. | |
| 2002/0103412 | A1* | 8/2002 | Trimmer | 600/16 |
| 2002/0133219 | A1 | 9/2002 | Barry | |
| 2005/0159790 | A1* | 7/2005 | Shalev | A61M 5/14276 607/45 |
| 2005/0159802 | A1 | 7/2005 | Furst et al. | |
| 2005/0277912 | A1* | 12/2005 | John | 604/890.1 |
| 2006/0204532 | A1* | 9/2006 | John | 424/422 |
| 2006/0224154 | A1 | 10/2006 | Shadduck et al. | |
| 2006/0232417 | A1 | 10/2006 | August et al. | |
| 2007/0005043 | A1* | 1/2007 | Anderson | 604/890.1 |
| 2007/0010702 | A1 | 1/2007 | Wang et al. | |
| 2007/0112327 | A1* | 5/2007 | Yun et al. | 604/500 |
| 2007/0135887 | A1 | 6/2007 | Maschke | |
| 2007/0156015 | A1* | 7/2007 | Gilad | A61B 1/00156 600/102 |
| 2007/0167702 | A1 | 7/2007 | Nasser et al. | |
| 2007/0208923 | A1* | 9/2007 | Russell | A61B 34/30 712/22 |
| 2007/0210786 | A1 | 9/2007 | Allen et al. | |
| 2008/0004595 | A1 | 1/2008 | Viswangthan et al. | |
| 2008/0021307 | A1 | 1/2008 | Freeman et al. | |
| 2008/0114227 | A1* | 5/2008 | Haar et al. | 600/347 |
| 2008/0312717 | A1* | 12/2008 | Gantz | A61N 1/36032 607/57 |
| 2009/0005859 | A1 | 1/2009 | Keilman | |
| 2009/0062639 | A1 | 3/2009 | Zurn | |
| 2009/0210032 | A1* | 8/2009 | Beiski et al. | 607/59 |
| 2010/0030185 | A1* | 2/2010 | Hood et al. | 604/500 |
| 2010/0181964 | A1* | 7/2010 | Huggins | H02J 17/00 320/108 |
| 2010/0185185 | A1* | 7/2010 | John | 604/892.1 |
| 2010/0280304 | A1* | 11/2010 | Zemlok | A61F 5/0059 600/12 |
| 2011/0022025 | A1* | 1/2011 | Savoie | A61M 5/14248 604/500 |
| 2011/0028807 | A1* | 2/2011 | Abreu | 600/321 |
| 2011/0077459 | A1* | 3/2011 | Rofougaran | 600/103 |
| 2011/0095720 | A1 | 4/2011 | Shacklette et al. | |
| 2011/0103681 | A1 | 5/2011 | Kelly | |
| 2011/0196505 | A1* | 8/2011 | Forsell | 623/23.65 |
| 2012/0303001 | A1* | 11/2012 | John | 604/892.1 |
| 2014/0277249 | A1* | 9/2014 | Connor | A61F 5/0026 607/40 |

OTHER PUBLICATIONS

Allan., Microelectronics: The Medical Industry's Mini Marvels, 5 pgs. 2011.
Allan., System-Level Applications make MEMS Ubiquitous, pp. 61-64, 2012.
Bonanomi, et al., Microelectromechanical systems for endoscopic cardiac surgery. 2003, vol. 126, No. 3, pp. 851-852.
Breit, Unlocking the Potential of RF MEMS with New Design Appraches, pp. 10-11, 2012.
Bridges., FDA: Stent Patients Face Blood Clot Risk, Associated Press, pp. 1-3, 2006.
Bridges, FDA: Heart Stents Don't Up Risk of Death, Associated Press, 2 pgs., 2006.
Broockman, FCC'S Secret Spectrum, pp. 84-85, 2012.
Buntz, Theoretical Physicist Michio Kaku Predicts the Future of Healthcare, 3 pgs., 2012.
Busch, Detecting Ions in Mass Spectrometers with the Faraday Cup, 6 pgs., 2011.
Canavan, Nanotechnology, the future, and the FDA Articles Drug Discovery and Development, 4 pgs, 2011.
Carey, No One Wanted to Hear, Business Week, Oct. 9, 2006, pp. 91-92.
CAT Scan (CT)—Body, download Mar. 19, 2009, pp. 1-6. http://www.radiologyinfo.org/en/info.cfm?PG=bodyct.
Chai., Atomic and Molecular Manipulation to Drive Development of Nanoscience, pp. 1, Jun. 2011.
Chatterjee., Driving toward milivolt electronics, pp. 22, 2011.
Chatterjee., Contributing Technical Editor. New devices for nanoelectronics., Mar. 3, 2011, pp. 18.
Criado et al, Talent LPS AAA stent graft: Results of a pivotal clinical trial, Journal of Vascular Surgery vol. 37, No. 4, 2006, pp. 1-10.
Comerford., Special namotubes may up Li battery's energy density—Electronic Products, 2011, pp. 2 pgs.
Cordes, et al., CMOS cameras allow robut active stabilization of laser beams. Aug. 2011, 3 pages.
Colin., SLI eliminates the need for touch in MEMS applications, pp. 16, 2012.
Deffree., Nanoscale pairings of particles show promise as miniaturized power sources, pp. 16, 2011.
Dente., M.D., Endovascular Repair for Aneurysm Rupture, VascularWeb, Provided by the Society for Vascular Surgery, vol. 2—2006 Issue 1.
Edamatsu, Entangled Photons: Generation, Observation, and Characterization. vol. 46, No. 11. 2007, pp. 7175-7187.
Edwards, et al., CT measurement of main pulmonary artery diameter, 1998, pp. 1018-1020.
Esfandyari et al., Integrated smart systems with MEMS sensors, pp. 12, 2012.
Engineering a Paradigm Shift in At-Home Monitoring Devices. Jun. 2011, pp. 4 & 6.
Evans., AAA Repair: Early Intervention or Wait and See?, VascularWeb,Provided by the Society for Vascular Surgery, vol. 2—2006 Issue 3.
Grace, et al., Why MEMS-based systems solutions? Significant reasons have caused MEMS suppliers to change their design approach, thus opening new market opportunities. 2011, pp. 17-19. Gilleo_MEMS_in-Medicine_August_2005_pp_1_3_pp_1_10.
Grace., MEMS-Based Systems Solutions Emerge for Analytical Instruments, pp. 32, 2012.
Grace., What's driving MEMS commercialization 4 pgs . . . 2011.
Hank Russell, CT Angiography Shows Promise in Arterial Imaging, VascularWeb, Provided by the Society for Vascular Surgery, vol. 2—2006 Issue 1.
Hank Russell, Imaging System Tested for Visualizing Stents, VascularWeb, Provided by the Society for Vascular Surgery, vol. 2—2006 Issue 1.
Hecht, The incredible shrinking laser makes a big impact. Oct. 2011, pp. 41-45.
http://universe-review.ca/I08-24-scintillator.jpg.
http://www.upei.ca/~phys221/MH/How_they_work_/how_they_work_.html.
http://images.search.yahoo.com/search/images/view?frame=top &back=http%3A%2F%F%2Fs . . .
Jayaraman, et al., 760 kHz OCT scanning possible with MEMS-tunable VCSEL. 2011, pp. 1-2.
Kastalsky, et al., Semiconductor high-energy radiation scintillation detector, pp. 650-656, 2006.
Kiourti., Biomedical Telemetry: Communication Between Implanted Devices and the External World. 2010, pp. 1-7.
Kotzara, et al., Evalution of MEMS materials of construction for implantable medical devices. 2002, pp. 2737-2750.
Lawton., Single-Use High Capacity Membrane Chromatography, pp. 30, 2012.
Lightman., Applying MEMS for quality of life, pp. 43-44, 2011.
Lesney,, Aortic Debranching Can Aid Endovascular Repair of TAA, VascularWeb, Provided by the Society for Vascular Surgery, vol. 2—2006 Issue 2.
Macneil., Stenting or Open Repair? EVAR, DREAM Trials Inconclusive, VascularWeb, Provided by the Society for Vascular Surgery ,vol. 2—2006 Issue 1.

(56) References Cited

OTHER PUBLICATIONS

MEMS in medical devices: the possibilities are endless. 2009, ppl 1-2.
New alloy suits MEMS devices, 3 pgs, 2012.
PEAKS of Interest, pp. 288, vol. 30, No. 4, Apr. 2012.
Reichenspurner et al., Use of the Voice-Controlled and Computer-Assistant Surgical, pp. 1, Jul. 1999.
Sadeg et al. Automated liquid-chromatographic analyzer used for toxicology screening in a general hospital, pp. 498-504, 1997.
Sawant., Enhancing Personal Health Monitoring Systems with FPGA Technology, pp. 4-6, 2012.
Seward., Fantastic voyage through the cardiovascular system. 2003, 5, pp. 8-11.
Shimizu et al., Easier to Swallow, pp. 14-15, 2012.
Swift et al, Reducing Size While Improving Functionality and Safety in Next-Generation Medical Device Design, pp. 14, 2012.
Taranovich., Medical Sensors Encompass Biomedical Electronics, 6. pgs, 2011.
Timothy F. Kirn, European Series: Carotid Stent vs. Endarterectomy, VascularWeb,Provided by the Society for Vascular Surgery ,vol. 2—2006 Issue 3.
Timothy F. Kirn, Endovascular Emergency Repair of Ruptured AAA Uses Balloon Technique, Vascular Web,Provided by the Society for Vascular Surgery ,vol. 2—2006 Issue 3.
Timothy F. Kirn, Endovascular AAA Repair Is Gaining, Expert Asserts, VascularWeb, Provided by the Society for Vascular Surgery ,vol. 1—2005 Issue 2.
Timothy F. Kirn, Endovascular Aortic Repair Less Harmful to Heart?, VascularWeb,Provided by the Society for Vascular Surgery ,vol. 2—2006 Issue 3.
Timothy J. Parker, Pixellated NaI(T1). For Enhanced Performance 2001, 2 pgs.
Tupta et al., Tools and techniques for testing Nanotech, pp. 85-89, 2011.
Veith, The Rush to Stent: A Cause for Concern, VascularWeb, Provided by the Society for Vascular Surgery, vol. 2—2006 Issue 2.
Weiler., High-power pico- and femtosecond lasers enable new applications. Oct. 2011, pp. 55-61.
Wireless, Self-Propelled Medical Implant on the Horizon, 2 pgs, 2012.
Woo., MD, Acute Aortic Dissection: A Case for Specialized Centers Colleague Commentary, VascularWeb, Provided by the Society for Vascular Surgery, vol. 2—2006 Issue 3.
Zimmermann et al., Robot-assisted Navigated Neuroendoscopy, Neurosurgery: vol. 51(6) Dec. 2002 pp. 1446-1452.
Bibber., Nanotech Redefines the way drug-delivery devices think, pp. 28, 39,41 & 42, 2012.
Greb., Reformulating Injectables for Oral Delivery, pp. 48,5052,54 & 56, 2011.
Hartford., Mushy Memory Has Biological Potential, pp. 22, 2011.
Hudson., Implantable nanochannel technology advances drug delivery, pp. 30,32,34,& 36, 2012.
Magnetic Responsive Hydrogel Material Delivery System, Air Force Reseach Laboratory, Ohio, pp. 26-27, 2012.
McCormick., Disappearing Act: Biocompatible Electronics Vanish when no longer needed, pp. 1-2, Sep. 27, 2012.
McDonald., Strategic IC Design for Implantables, pp. 43-46, 2012.
Motor Driver encoder controller, Purdue University West Lafayette, IN, pp. 23-24, 2012.
Nelson., Product Innovations Aid MEMS Design and Test, pp. 26,28 & 30, Feb. 2013.
Nickolas., Chip implant promises tumor monitoring, pp. 11, 2011.
Pearce., Vascular Voyage, pp. 17-18, 2012.
Study, Tim., Are Nanomaterials Safe or Not?, pp. 6, 2012.
Thryft., First Robot-Guided Brain Surgery Performed, pp. 1, 2012.
Wickes., Barriers to Adopting, New intelligent data management systems combat mobile netwo . . . pp. 14-15, 2012.
Nguyen, "RF MEMS for wireless applications", Device Research Conference, 2002, Abstract.
Nguyen, "RF MEMS for wireless applications", Conf. Digest, 2002, Device Research Conference, Santa Barbars, California, Jun. 24-26, 2002, pp. 9-12.
Sekitani et al., "A large-area wireless power-transmission sheet using printed organic transistors and plastic MEMS switches", Nature Materials 6, 413-417 (2007).
Lal et al., "A Nuclear Battery for MEMS Devices", University of Wisconsin, Madison, 2001. pp. 1-12.
Lal et al., "The Daintiest Dynamos", IEEE Spectrum, 2004, pp. 36-41.
Hirota et al., "Proposal for Electric Power Generation by Using X-Rays and Gamma Rays", Journal of Nuclear Science and Technology, vol. 48, No. 1, pp. 103-106 (2011).
Penn Medicine, "Gamma Knife"—1968, pennmedicine.org.

\* cited by examiner

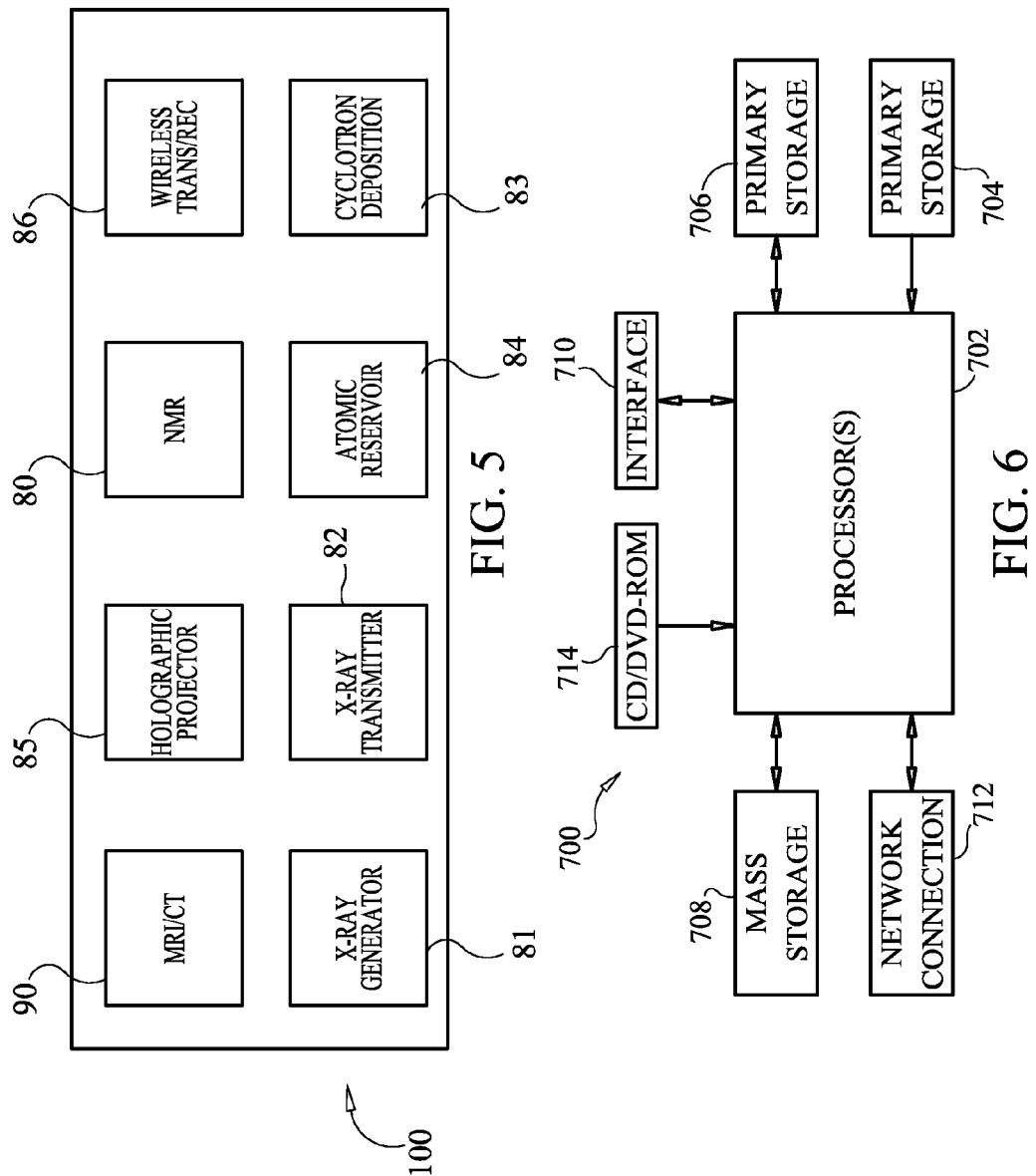

MODULE FOR TREATMENT OF MEDICAL CONDITIONS; SYSTEM FOR MAKING MODULE AND METHODS OF MAKING MODULE

FIELD OF THE INVENTION

The field of the present invention relates to the delivery and useful placement of medical devices and medicine; materials within the human body. This field of the invention specifically relates to the insertion of biological material, as well as non-biological devices where placement of a device is used to repair physiological deficiencies or enhance conditions in the human body. The field of the invention relates generally to devices useful for delivering medical agents to patient tissues, and in one particular aspect to medical delivery devices such as needles that deliver medicines to regional areas of the human body.

BACKGROUND OF THE INVENTION

Many needle devices in current use transfer a single stream of medical agent, and either arrange a focused delivery of the agent, or require frequent repositioning to distribute the agent through a volume of tissue. Repeated positioning of a device can cause discomfort to the patient and can lead to extended tissue damage.

Additionally, current devices and methods for delivering medical agents can cause localized pressure as the agent is delivered, making delivery of additional amounts of the agent more difficult and potentially causing other patient-related complications.

In view of this background of current devices, requirements remain for improved or alternative medical agent delivery devices and methods, including, for example those that facilitate regional delivery of the agent and/or reduce complications which may arise due to pressure increases in the immediate and/or surrounding tissues. The present invention provides embodiments addressed to these and other needs.

SUMMARY OF THE INVENTION

In one aspect of the present invention, a module producible inside a living body is provided, the module comprising: an instructions receiver configured to receive wireless transmissions of instructions from a master controller located outside of the body when the module is inside the body; an energy receiver configured to receive wireless transmission of non-destructive energy from the master controller located outside of the body when the module is inside the body; a battery; and a communications and guide element electrically connected to the instructions receiver, the energy receiver and the battery.

In at least one embodiment, the module further includes at least one positioning element configured to be tracked by the master controller, so that the master controller can identify location and orientation of the module.

In at least one embodiment, the module further includes an electronic interface configured to convert energy from the energy receiver to electric energy to charge the battery.

In at least one embodiment, the energy receiver is configured to receive X-ray energy from the master controller.

In at least one embodiment, the module further includes an atom receiving unit configured to receive at least one of: atoms, atoms and molecules, molecules, molecules and compounds, or compounds from a location outside of the body while the module is inside the body, the atoms, atoms and molecules, molecules, molecules and compounds, or compounds being transmitted transdermally through the body.

In at least one embodiment, the module further includes an atom receiving unit configured to receive at least one of: atoms, atoms and molecules, molecules, molecules and compounds, or compounds from a location outside of the body while the module is inside the body, the atoms, atoms and molecules, molecules, molecules and compounds, or compounds being transmitted through tissue of the body to arrive a location of the atom receiving unit in the module inside the body.

In at least one embodiment, the module further includes a chemical reaction unit in fluid communication with the atom receiving unit, the chemical reaction unit being configured to receive the atoms, atoms and molecules, molecules, molecules and compounds, or compounds from the atom receiving unit and carry out a reaction of the atoms, atoms and molecules, molecules, molecules and compounds, or compounds to produce a treatment material.

In at least one embodiment, the module further includes an analysis chamber in fluid communication with the chemical reaction unit, the analysis chamber configured to receive the treatment material from the chemical reaction unit and chemically analyze the treatment material.

In at least one embodiment, the analysis chamber comprises a chromatography unit configured to chemically analyze the treatment material by chromatography.

In at least one embodiment, the module further includes an output chamber in fluid communication with the analysis chamber, the output chamber having at least one gate openable to place the output chamber in fluid communication with a location external of the module and closable to close off fluid communication with the location external of the module, wherein after the treatment material within the analysis chamber is analyzed and determined to be acceptable, the output chamber receives the treatment material from the analysis chamber.

In at least one embodiment, the output chamber is configured to close off fluid communication with the analysis chamber after receiving the treatment material, and expel the treatment material to the location outside the module after opening the at least one gate.

In at least one embodiment, the module further includes a field programmable gate arrays (FPGA) configured to be reprogrammable to change functions of the module, wherein the reprogramming is performable from a location outside of the body while the module is inside the body.

In at least one embodiment, the module further includes at least one gate interposed between the output chamber and the analysis chamber; at least one gate interposed between the analysis chamber and the chemical reaction unit; and at least one gate interposed between the chemical reaction unit and the atom receiving unit; wherein each of the gates is configured to open to allow fluid communication between the respective chambers and/or units that it is interposed, and wherein each of the gates is further configured to close to prevent fluid communication between the respective chambers and/or units that it is interposed.

In at least one embodiment, the module further includes at least one pressure transducer located in each of the atom receiving unit, chemical reaction unit, analysis chamber and output chamber.

In another aspect of the present invention, a at least one embodiment, a system for treatment of a condition within a living body is provided, the system including: a master controller located outside of the body; and a module producible inside the body by the master controller.

In at least one embodiment, the module comprises an atom receiving unit and the master controller comprises a cyclotron and an atomic reservoir configured to feed at least one of atoms, atoms and molecules, molecules, molecules and compounds, or compounds to the cyclotron, the wherein the cyclotron is configured to deliver the atoms, atoms and molecules, molecules, molecules and compounds, or compounds within a beam to the atom receiving unit, from a location outside of the body, through tissue of the body and to the atom receiving unit.

In at least one embodiment, the master controller further comprises a holographic projector configured to produce a three dimensional holographic blueprint superimposable on a surgical target in the body, wherein the holographic blueprint is followed by the master controller to produce the module in the body at a location of the surgical target.

In at least one embodiment, the master controller produces the module atom-by-atom.

In at least one embodiment, the master controller is configured to drive, as well as hold a current position and orientation of the module using magnetic forces.

In at least one embodiment, the module comprises at least one guide element detectable by the master controller to indicate location and orientation of the module.

In at least one embodiment, the module comprises a module instructions receiver and the master controller comprises a master instructions transmitter, the master instructions transmitter configured to transmit wireless instructions to the module instructions receiver when the master controller is located outside of the body and the module is inside the body; and the module comprises a module transmitter and the master controller comprises a master receiver, the module transmitter configured to transmit wireless transmissions to the master transmissions receiver when the master controller is located outside of the body and the module is inside the body.

In at least one embodiment, the master controller comprises a non-destructive energy generator and a non-destructive energy transmitter, and the module comprises a non-destructive energy receiver configured to receive non-destructive energy transmitted by the non-destructive energy transmitter when the master controller is located outside of the body and the module is inside the body.

In at least one embodiment, the module further comprises an energy converter configured to convert the non-destructive energy received to electrical energy; and a battery configured to be charged by the electrical energy.

In at least one embodiment, the module comprises: a chemical reaction unit is fluid communication with the atom receiving unit, the chemical reaction unit being configured to receive the atoms, atoms and molecules, molecules, molecules and compounds, or compounds from the atom receiving unit and carry out a reaction of the atoms, atoms and molecules, molecules, molecules and compounds, or compounds to produce a treatment material.

In another aspect of the present invention, a method of producing a module inside a body of a patient is provided, the method including: providing a master controller at a location outside of the body of the patient; transmitting at least one of at least one of atoms, atoms and molecules, molecules and compounds, or compounds from the master controller at the location outside of the body, through tissue of the body and to a surgical target location inside of the body; and reacting the atoms, atoms and molecules, molecules, molecules and compounds, or compounds to produce the module.

In at least one embodiment, the method further includes: projecting a three dimensional holographic blueprint over the surgical target location; and producing the module by following the blueprint as a guide.

In at least one embodiment, the module is produced in stages.

In at least one embodiment, a first stage includes producing: an instructions receiver configured to receive wireless transmissions of instructions from the master controller located outside of the body when the module is inside the body; an energy receiver configured to receive wireless transmission of non-destructive energy from the master controller located outside of the body when the module is inside the body; a battery; and a communications and guide element electrically connected to the instructions receiver, the energy receiver and the battery.

In at least one embodiment, a second stage comprises producing: an atom receiving unit configured to receive at least one of: atoms, atoms and molecules, molecules, molecules and compounds, or compounds from a location outside of the body while the module is inside the body; and a chemical reaction unit in fluid communication with the atom receiving unit, the chemical reaction unit being configured to receive the atoms, atoms and molecules, molecules, molecules and compounds, or compounds from the atom receiving unit and carry out a reaction of the atoms, atoms and molecules, molecules, molecules and compounds, or compounds to produce a treatment material.

In at least one embodiment, the second stage further comprises producing: an analysis chamber in fluid communication with the chemical reaction unit, the analysis chamber configured to receive the treatment material from the chemical reaction unit and chemically analyze the treatment material; and an output chamber in fluid communication with the analysis chamber, the output chamber having at least one gate openable to place the output chamber in fluid communication with a location external of the module and closable to close off fluid communication with the location external of the module, wherein after the treatment material within the analysis chamber is analyzed and determined to be acceptable, the output chamber receives the treatment material from the analysis chamber.

In another aspect of the present invention, a method of treating the body of a patient is provided, the method including: providing a master controller at a location outside of the body of the patient; transmitting at least one of at least one of atoms, atoms and molecules, molecules, molecules and compounds, or compounds from the master controller at the location outside of the body, through tissue of the body and to a surgical target location inside of the body; reacting the atoms, atoms and molecules, molecules, molecules and compounds, or compounds to produce a module; transmitting at least one of at least one of atoms, atoms and molecules, molecules, molecules and compounds, or compounds from the master controller at the location outside of the body, through tissue of the body and to an atom receiving unit in the module located inside of the body; reacting the atoms, atoms and molecules, molecules, molecules and compounds, or compounds in the module to produce a treatment material; and driving the treatment material out of the module to a treatment area in a vicinity of the surgical target location.

In at least one embodiment, the method further includes analyzing the treatment material after the reacting; performing the driving step when results of the analyzing are acceptable; and preventing the driving step from being performed when the results of the analyzing fail to be acceptable.

In at least one embodiment, the method further includes performing at least one of: encapsulating the module, removing the module, or dissipating the module when the results of the analyzing fail to be acceptable.

These and other and features of the invention will become apparent to those persons skilled in the art upon reading the details of the modules, systems and methods as more fully described below.

BRIEF DESCRIPTION OF THE DRAWINGS

The forgoing aspects and many of the attendant advantages of the present invention will become more readily apparent in the following detailed description and accompanying drawings, wherein:

FIG. 5 is a schematic illustration of hardware components included in system 100 according to an embodiment of the present invention.

FIG. 6 is a block diagram of a computer system that may be implemented in a system according to an embodiment of the present invention.

DETAILED DESCRIPTION OF THE INVENTION

Figure 1:
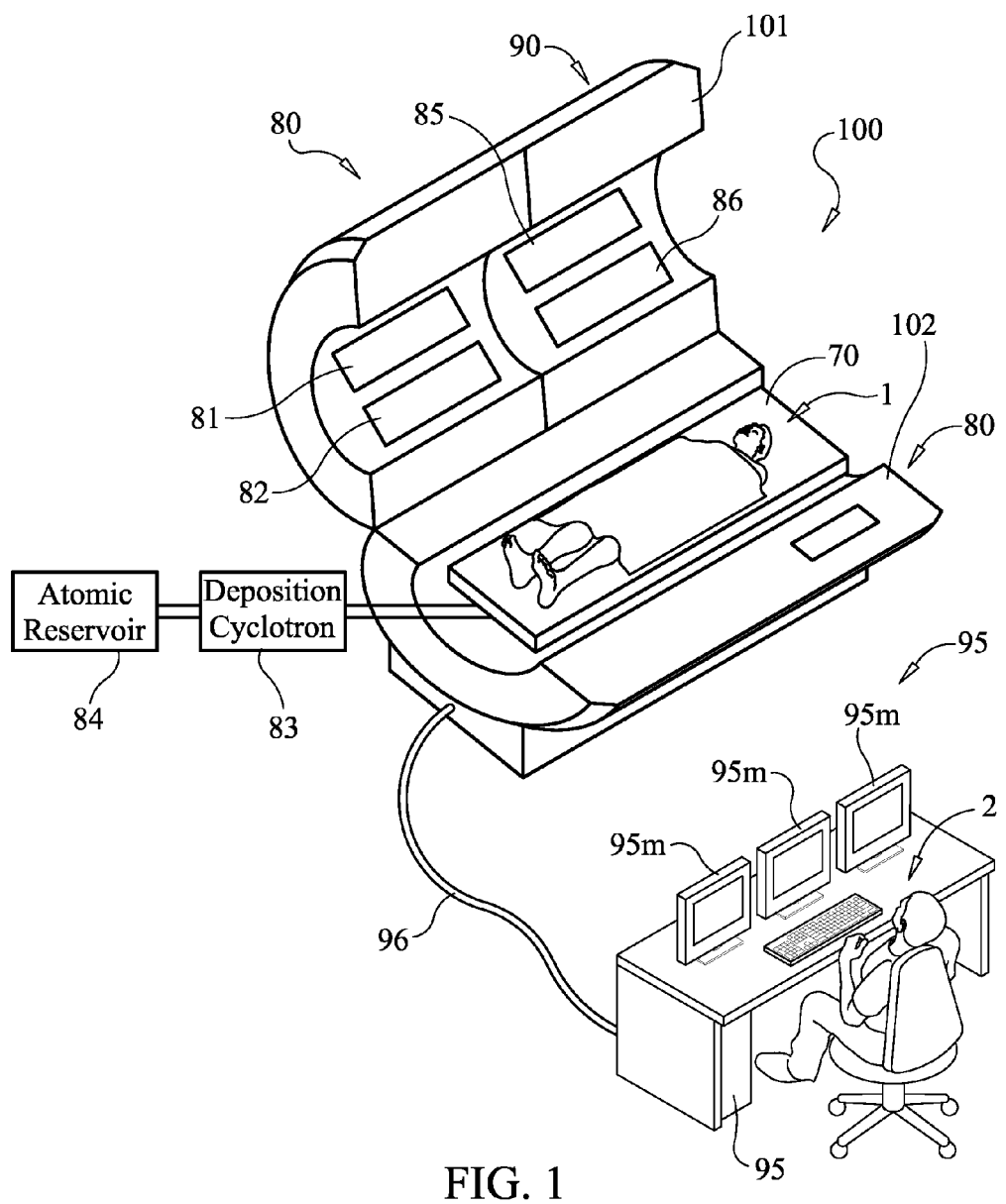
FIG. 1 schematically illustrates a master machine according to an embodiment of the present invention, and a patient thereon.

Before the present systems, modules and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a module" includes a plurality of such modules and reference to "the battery" includes reference to one or more batteries and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "patient" herein refers to a human patient who may be an adult or child, male or female. Further, the term patient, as used herein, includes mammalian species of all types, genders and developmental stages, and may extend to various other vertebrates.

"Nanotechnology" generally refers to technology relating to structures sized between about 1 to about 100 nanometers in at least one dimension, and involves developing materials or devices within that size. Quantum mechanical effects are very important at this scale. Nanotechnology is very diverse, fluctuating from enlargement of conventional device physics to completely new approaches based upon molecular self-assembly, from flourishing new materials with dimensions on the nanoscale to exploring whether one can directly control matter on the atomic scale.

"Micro-Electro-Mechanical Systems" (MEMS), involves the integration of mechanical elements, sensors, transducers, actuators, and electronics on a common silicon substrate through microfabrication technology. While the electronics are fabricated using integrated circuit (IC) process sequences (e.g., CMOS (Complementary Metal Oxide Semiconductor), Bipolar, or BICMOS (BIpolar Complementary Metal Oxide Semiconductor) processes), the micromechanical components are fabricated using compatible "micromachining" processes that selectively etch away parts of the silicon wafer or add new structural layers to form the mechanical and electromechanical devices. Microelectromechanical systems (MEMS) (also written as micro-electro-mechanical, MicroElectroMechanical or microelectronic and microelectromechanical systems) is the technology of very small mechanical devices driven by electricity; it merges at the nano-scale into nanoelectromechanical systems (NEMS) and nanotechnology.

MEMS are made up of components between around 1 to 100 micrometers in size (i.e. 0.001 to 0.1 mm) and MEMS devices generally range in size from about 20 micrometers (20 millionths of a meter) to a millimeter. They usually include a central unit that processes data, the microprocessor, and several components that interact with the outside such as microsensors. The following materials have been used to construct MEMS devices, single crystal silicon (Si), polycrystalline silicon (polysilicon), silicon oxide (SiO2), silicon nitride (Si3N4), single crystal cubic silicon carbide (3C—SiC or b-SiC), titanium (Ti).

An "integrated circuit" (IC) is an electronic circuit manufactured by the patterned diffusion of trace elements into the surface of a thin substrate of semiconductor material. Integrated circuits (IC) are constructed of semiconducting materials, which are midway between good conductors, like copper, and insulators such as plastic. Silicon is the current favorite. Ultrapure silicon is mixed with small, precise amounts of other elements to create electronic materials with different characteristics. Additional materials are deposited and patterned to form interconnections between semiconductor devices. Integrated circuits may be small squares of silicon, imprinted with microscopic patterns. The patterns may contain hundreds of millions of transistors, resistors and other electronic parts.

"Nuclear Magnetic Resonance" (NMR) was described independently by Felix Bloch and Edward Mills Purcell in 1946, both of whom shared the Nobel Prize in physics in 1952, for their discovery. The development of NMR as a technique of analytical chemistry and biochemistry parallels the development of electromagnetic technology. This technique allows the detection of radio frequency energy, and the absorption of such energy by matter.

"Computerized Axial Topography (CAT)/CT (computed tomography), sometimes called CAT scan, uses special X-ray equipment to obtain image data from different angles around the body and then uses computer processing of the information to show a cross-section of body tissues and organs. Recent technical advances with respect to CT scanners now enable 192 images of the body per second. This non-invasive, virtually pain-free procedure offers exceptional image quality, which can mean better diagnosis, faster recovery time and increased patient comfort and convenience.

"Internet Protocol Packet" (IP Packet) is the smallest message entity exchanged via the Internet Protocol across an Internet Protocol version 6 (IPv6) network. Packets consist of control information for addressing and routing, and a payload consisting of user data. The control information in IPv6 packets is subdivided into a mandatory fixed header and optional extension headers. The payload of an IPv6 packet is typically a datagram or segment of the higher-level Transport Layer protocol, but may be data for an Internet Layer (e.g., ICMPv6) or Link Layer (e.g., OSPF) instead.

"Magnetic Resonance Imaging" (MRI) is a unique imaging method because, unlike the usual radiographs (X-rays), radioisotope studies or even Computed Tomography (CT) scanning, it does not rely on ionizing radiation. Instead radio frequency waves are directed at protons, the nuclei of hydrogen atoms, in a strong magnetic field. The protons are first "excited" and then "relaxed," emitting radio signals that can be computer-processed to form an image. In the body, protons are most abundant in the hydrogen atoms of water—the "H"'s of $H_2O$—so that an MRI image shows differences in the water content and distribution in various body tissues.

"Nuclear Scans": in some instances, a doctor may request that someone have a nuclear scan. A nuclear scan involves only a small "tracer" dose of radioactive material, and is not dangerous. Once this tracer element is injected into a patient's system, it can be followed through the system as the patient lies directly underneath a sensing device. A nuclear scan is most often used to assess body function. Other uses include measurement of stomach emptying and localization of intestinal bleeding. Nuclear scans require very little preparation.

"Chromatography" is a technique used to analyze mixtures and substances. Chromatography can be used to monitor the progress of a reaction, identify compounds present in a given mixture, and determine the purity of a substance. Since the 1950's, gas chromatography (GC) has been a common approach for analysis of volatile mixtures in which the components are differentiated in space and time. Conventional GCs tend to be large, fragile, and relatively expensive table-top instruments with high power consumption, but they are known to deliver accurate and selective analysis. The use of MEMS technology for GC development is a promising approach to micro-instruments having lower cost, smaller size, lower power consumption, faster analysis, and greatly increased portability for in-field use. Such systems will make gas chromatography a pervasive method for analysis, with applications related to biomedical diagnostic procedures.

"X-radiation" (composed of X-rays) is a form of electromagnetic radiation. X-rays have a wavelength in the range of 0.01 to 10 nanometers, corresponding to frequencies in the range 30 petahertz to 30 exahertz ($3 \times 10^{16}$ Hz to $3 \times 10^{19}$ Hz) and energies in the range 120 eV to 120 keV. They are shorter in wavelength than UV rays and longer than gamma rays. In many languages, X-radiation is called Röntgen radiation, after Wilhelm Conrad Röntgen, who is usually credited as its discoverer, and who had named it X-radiation to signify an unknown type of radiation.

Correct spelling of X-ray(s) in the English language includes the variants X-ray(s) and X ray(s). XRAY is used as the phonetic pronunciation for the letter x. X-radiation used in the present invention is "non-destructive X-radiation" (X-ray energy) that doesn't significantly destroy or damage human tissue, such as the X-ray energy typically used for performing chest X-ray imaging, dental imaging, fluoroscopy and the like.

Holography is a technique, which enables three-dimensional images to be made. It involves the use of a laser, interference, diffraction, light intensity recording and suitable illumination of the recording. The image changes as the position and orientation of the viewing system changes in exactly the same way as if the object were still present, thus making the image appear three-dimensional.

"FPGA": A Field-programmable Gate Array (FPGA) is an integrated circuit designed to be configured by the customer or designer after manufacturing—hence "field-programmable". The FPGA configuration is generally specified using a hardware description language (HDL), similar to that used for an application-specific integrated circuit (ASIC) (circuit diagrams were previously used to specify the configuration, as they were for ASICs, but this is increasingly rare). FPGAs can be used to implement any logical function that an ASIC could perform. The ability to update the functionality after shipping, partial re-configuration of the portion of the design and the low non-recurring engineering costs relative to an ASIC design (notwithstanding the generally higher unit cost), offer advantages for many applications.

FPGAs contain programmable logic components called "logic blocks", and a hierarchy of reconfigurable interconnects that allow the blocks to be "wired together"—somewhat like many (changeable) logic gates that can be interwired in (many) different configurations. Logic blocks can be configured to perform complex combinational functions, or merely simple logic gates like AND and XOR. In most FPGAs, the logic blocks also include memory elements, which may be simple flip-flops or more complete blocks of memory.

"Stem cells" are biological cells found in all multicellular organisms, that can divide through mitosis and differentiate into diverse specialized cell types and can self-renew to produce more stem cells. In mammals, there are two broad types of stem cells: embryonic stem cells that are isolated from the inner cell mass of blastocysts, and adult stem cells that are found in various tissues. In adult organisms, stem cells and progenitor cells act as a repair system for the body, replenishing adult tissues. In a developing embryo, stem cells can differentiate into all the specialized cells, but also maintain the normal turnover of regenerative organs, such as blood, skin, or intestinal tissues.

A "cyclotron" is a type of particle accelerator. In physics, the cyclotron frequency or gyrofrequency is the frequency of a charged particle moving perpendicularly to the direction of a uniform magnetic field, i.e. a magnetic field of constant magnitude and direction. Since that motion is always circular, the cyclotron frequency is well defined.

Cyclotrons accelerate charged particles using a high-frequency, alternating voltage (potential difference). A perpendicular magnetic field causes the particles to spiral almost in a circle so that they re-encounter the accelerating voltage many times.

"Chemical vapor deposition" (CVD) is a chemical process used to produce high-purity, high-performance solid materials. The process is often used in the semiconductor industry to produce thin films. In a typical CVD process, the wafer (substrate) is exposed to one or more volatile precursors, which react and/or decompose on the substrate surface to produce the desired deposit. Frequently, volatile by-products are also produced, which are removed by gas flow through the reaction chamber.

Microfabrication processes widely use CVD to deposit materials in various forms, including: monocrystalline, polycrystalline, amorphous, and epitaxial. These materials include: silicon, carbon fiber, carbon nanofibers, filaments, carbon nanotubes, $SiO_2$, silicon-germanium, tungsten, silicon carbide, silicon nitride, silicon oxynitride, titanium nitride, and various high-k dielectrics. The CVD process is also used to produce synthetic diamonds.

"Chemical reaction engineering" ("reaction engineering" or "reactor engineering") is a specialty in chemical engineering or industrial chemistry dealing with chemical reactors. Frequently the term relates specifically to catalytic reaction systems where either a homogeneous or heterogeneous catalyst is present in the reactor. Sometimes a reactor per se is not present by itself, but rather is integrated into a process, for example in reactive separations vessels, retorts, certain fuel cells, and photocatalytic surfaces.

Chemical reaction engineering aims at studying and optimizing chemical reactions in order to define the best reactor design. Hence, the interactions of flow phenomena, mass transfer, heat transfer, and reaction kinetics are of prime importance in order to relate reactor performance to feed composition and operating conditions. Although originally applied to the petroleum and petrochemical industries, its general methodology combining reaction chemistry and chemical engineering concepts allows to optimize a variety of systems where modeling or engineering of reactions is needed. Chemical reaction engineering approaches are indeed tailored for the development of new processes and the improvement of existing technologies.

Chemical reaction engineering as a discipline started in the early 1950's under the impulse of researchers at the Shell Amsterdam research center and the University of Delft. The term chemical reaction engineering was apparently coined by J. C. Vlugter while preparing the 1st European Symposium on Chemical Reaction Engineering which was held in Amsterdam in 1957.

"Guide, control instructions RF energy", as used herein, refers to wireless RF signals used to control a module as described herein. For example, wireless RF instructions can be sent from a master NMR machine instruction transmitter to an instruction receiving unit of a module.

DETAILED DESCRIPTION

FIG. 1 schematically illustrates a master machine 100 according to an embodiment of the present invention. A patient 1 is positioned on a table 70 of the master machine 100, with elements of an NMR (nuclear magnetic resonance) apparatus 80 below and above him/her. The patient 1 is almost fully enclosed by the CT/MRI (computerized tomography/magnetic resonance imaging) apparatus 90, NMR apparatus 80 and other associated equipment, X-ray generator 81 X-ray transmitter 82, holographic projector 85. The X-ray generator 81 and the X-ray transmitter 82 technology are currently available as known to those of ordinary skill in the art.

The system 100 has a clamshell arrangement/configuration with the forward portion 90 of the upper clamshell 101 containing CT/MRI equipment, which, in combination with NMR equipment 80 in the rearward portion of system 100 is configured to perform CT/MRI and nuclear magnetic resonance functions. Both CT/MRI and NMR machinery are currently available as known to those of ordinary skill in the art. The upper clamshell 101 is configured to move back and forth (forwardly and rearwardly) over the patient 1 and relative to the lower clamshell 102 in directions toward the head (forward) and the feet (rearward) of the patient 1, so that either portion 80 or 90 can be located over any desired location of the patient 1.

The instruction transmission and receiving element 86 is a subsection of the forward portion 90 of the top clam shell 101. The top clam shell 101 further contains X-ray generation element 81 and X-ray transmission element 82. The wireless instruction transmission/receiving element 86 sends wireless instructions to fabricate, to guide and control a module 10, which is discussed below in further detail. The wireless instruction transmit/receiving unit 19, on the module 10 (e.g., see FIGS. 2A-2F), receives and transmits the wireless instructions from the transmission/receiving module 86 and transfers the instructions to the various units of module 10. Wireless transmission and receiving technology are currently available as known to those of ordinary skill in the art.

The combination cyclotron and chemical vapor deposition element 83 is also contained beneath the patient in the master system 100. Because module 83 is not visible in FIG. 1, as obstructed by table 70, it is shown schematically adjacent the master machine 100, but in practice, it is to be understood that it is connected and mounted in the lower clam shell 102 beneath the table 70. The cyclotron and chemical vapor deposition technology are currently available as known to those of ordinary skill in the art.

The three dimensional holographic projector 85 is located in the top clam shell 101 of system 100. Projector 85 produces a three dimensional holographic blueprint that is super imposed on the surgical target, and the module 10 is built atom-by-atom by use of the combination of the cyclotron and chemical vapor deposition chamber 83 contained beneath the patient in the system 100. Three dimensional holographic projection technologies are currently available as known to those of ordinary skill in the art.

The atomic reservoir 84 contains the necessary elementary atoms, molecules, etc., required for the procedure. The containers can be easily exchanged out based on the required atoms, molecules, etc. The atomic reservoir could be gas canisters, for oxygen, hydrogen or nitrogen. The atomic reservoir could be a solid container for elements such as: carbon, copper, iron or other solid type elements. The atomic reservoir could contain simple or complex molecules. The atomic reservoir's container depends upon the type of elements, atoms or molecules required. Typically atoms/molecules would be broken down to their simplest form and placed in containers and positioned in the atomic reservoir 84. The atomic reservoir is a dispensing device for supplying measured quantities of atoms/molecules to the deposition cyclotron.

FIG. 1 also illustrates an operator 2 operating the master computer 95. Multiple monitors 95M may be provided to indicate activities of the ongoing procedure, as there will generally be a need to track multiple activities at one time. However, the present invention is not limited to use of multiple monitors 95M as other embodiments may employ just one monitor 95M.

Figure 2A:
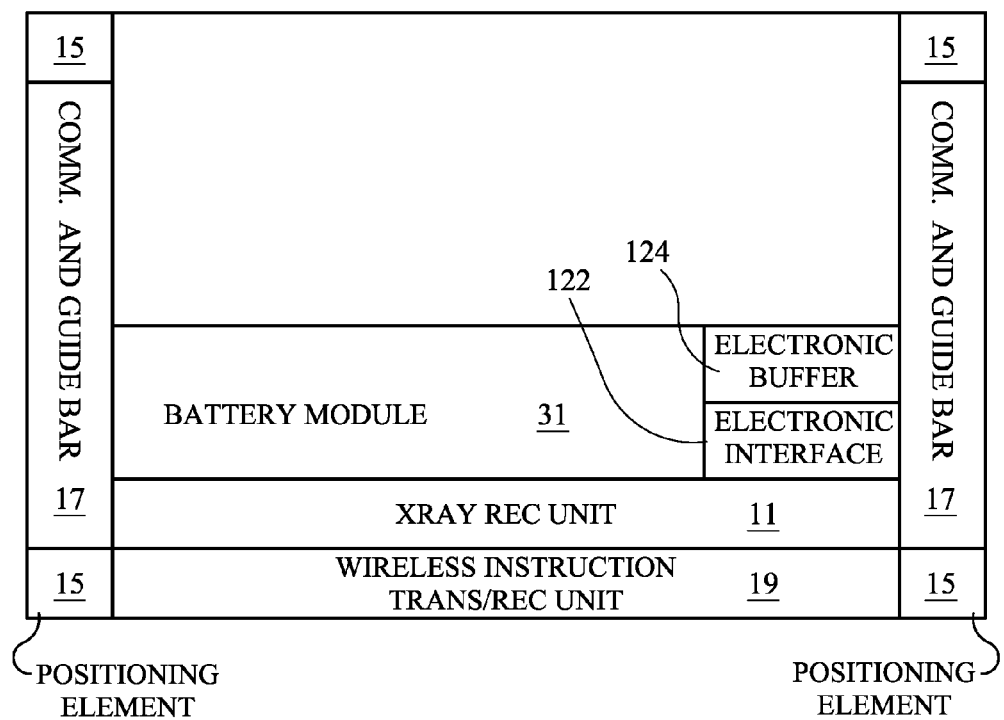
FIG. 2A is a schematic illustration of the beginning stages (first phase) of fabricating a module according to an embodiment of the present invention.

These elements of the system 100 allow the three dimensional holographic projection technologies 85, with respect to the construction and controlled fabrication of the module 10 (schematically illustrated in FIG. 2a). During the three dimensional holographic projection procedure, process communication information is transmitted to the module 10.

FIG. 2A is a schematic illustration of the beginning stages (first phase) of fabricating the module 10 according to an embodiment of the present invention. The module 10 is built in stages, atom-by-atom, to ensure the proper functioning of the module 10. Module 10 is fabricated using a combination of MEMS technology and integrated circuit technology. Module 10 includes multiple sub-sections/units. The three dimensional holographic blueprint of the module is super imposed on the surgical target and the module is built atom-by-atom by use of the combination of the deposition/cyclotron element 83. After the first phase of fabricating the module 10, if it is determined the module 10 is non-functioning; the module 10 is encapsulated in bio-compatible material to protect the human body from any harmful effects of the non-functioning module 10 remaining within the human body indefinitely. Also, a non-functioning module can be surgically removed, if necessary. In addition, as technology improves, forces outside of the body can dissolve the module within the human body without lasing harm to the body.

The X-ray receiving unit 11 receives non-destructive X-ray energy from the X-ray transmitting element 82, which transmits the X-ray energy emitted by X-ray generation element 81. Transmitting element 82 is focused on the module 10 and then emits the X-rays in a focused delivery to module 10, where they are received by X-ray receiving unit 11.

The module battery 31 is fabricated during the first phase of construction of the module 10. The functionality of the module battery 31 will be tested after each phase of the construction of the module 10. The module battery 31 is connected to all module units with circuitry within the module 10 by use of the communication and guide bar 17 and the circuitry within the module 10. Battery fabrication technology is currently available as known to those of ordinary skill in the art.

The module battery 31 powers the module 10 at all times. The module battery 31 is charged using the electrical energy from the electronic interface 122 and the electronic buffer 124. The electronic interface 122 converts the X-ray energy to electrical energy. The electronic buffer (could be called "electronic buffer amplifier) 124 prevents interferences from the electronic interface 122 from affecting the module battery and vice versa. In this embodiment, the electronic interface 122 acts as a first stage, and the module battery 31 acts as a second stage.

The communication and guide bar 17 contains a structure, similar to a computer bus structure, which links all of the units within the module 10. Elements 122 and 124 are fabricated during phase one of the construction of the module 10. The X-ray transmitting element 82 sends X-ray energy (non-destructive) to the X-ray receiving unit 11 and the instructions transmission/receiving unit 86 sends and receives wireless instructions to instruction receiving unit 19 within the module 10.

The electronic power from the electronic buffer 124 is connected to the guide bar, communications bus (17). The electronic power is connected to all units within the module 10.

Communication and guide bar 17 is provided on two opposite sides of module 10 as illustrated in FIG. 2A. Redundancy is present by providing a pair of bars 17 to ensure optimum functioning and communication within the module 10. The communication and guide bar 17 also provides markers for motion control and movement of the module later on if the module must be moved within the human body. The positioning elements (physical positioning) 15 are constructed in alignment with holographic markers in a three dimensional holographic overlay that is superimposed over the appropriate surgical location where the module is to be positioned in the patient. Thus during fabrication of the module 10, the physical positioning elements are constructed where indicated by the hologram, inside the patient. Physical elements 15 are used the same way as described in the artery clearing and mucus clearing patent applications (i.e., see U.S. patent application Ser. Nos. 13/356,884 and 13/569,204, both of which are hereby incorporated herein, in their entireties) to guide and control the movement of the module 10 in case it must be moved or repositioned. Physical elements 15 enable a method of keeping track of the location of the physical module 10 within the body. Physical elements 15 may include, but are not necessarily limited to: radiopaque and/or radioactive material. In contrast, the holographic markers are not physical, the holographic markers provide a three dimensional guide as to the location as to where to fabricate the module 10. In at least one embodiment, the physical elements (also referred to as positioning elements) 15 contain a small "tracer" dose of radioactive material, and are not dangerous. This tracer dose allows for the comprehension of the precise location of the module 10 by the master machine 100 during and after fabrication of the module 10.

Figure 2B:
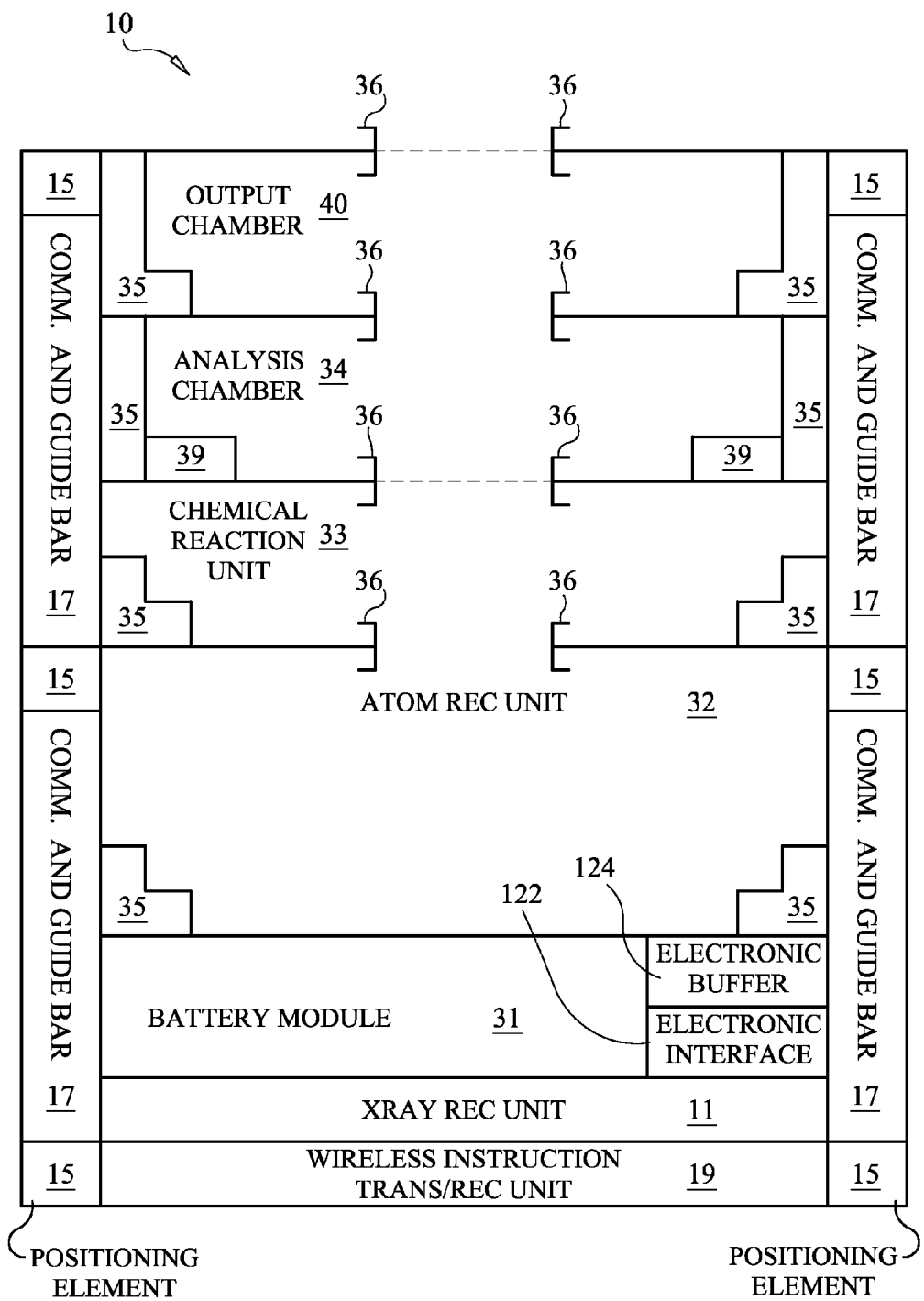
FIG. 2B is a schematic illustration of the second phase of fabricating a module according to an embodiment of the present invention.

Now turning to FIG. 2B, a schematic illustration of the second phase of fabricating the module 10 according to an embodiment of the present invention is shown. After the second phase of fabricating the module has been completed, if it is determined the module 10 is non-functioning; the module 10 is encapsulated in bio-compatible material to protect the human body from any harmful effects of the non-functioning module 10 remaining within the human body indefinitely. The encapsulation is performed if any aspect of the module 10 produced thus far is non-functioning, after testing remotely via the master computer 95. For example, if the electronic interface doesn't convert the X-rays to electrical energy and/or if the electronic buffer doesn't work and/or if the battery doesn't supply adequate power to the module 10 and/or if the atom receiving unit doesn't function properly, or if the module is otherwise determined to be nonfunctioning, the encapsulation is performed. Alternatively, the module can be removed or dissipated under any of these conditions or if the module is otherwise determined to be nonfunctioning. The encapsulation material is projected down to the module and built around the module atom-by-atom or molecule-by-molecule. The encapsulation material is a biocompatible material such as, but not limited to silicone, other polymers, silver, etc. As noted, a non-functioning module 10 can be surgically removed if leaving the module 10 within the body for long term is considered harmful to the body. In addition, as technology improves, forces outside of the body can dissolve the module within the human body without lasing harm to the body.

Additionally, with respect to FIG. 2B, this schematic illustrates the circuitry added during the second phase of fabricating the module 10. This schematic illustrates the circuitry, showing the added length of the communication and guide bar 17. Additional positioning elements 15 are added during this phase, they provide supplementary placement guides for the three dimensional holographic overlays projected from the holographic projector 85 to ensure proper placement of the three dimensional holographic overlay. The communication and guide bar 17 also provides additional markers 15 for motion control and movement of the module later on if the module must be moved within the human body after the module is fabricated. Module 10 is fabricated using a combination of MEMS technology and integrated circuit technology The atom receiving unit 32, the chemical reaction unit 33, the analysis chamber 34, and the output chamber 40 are added during the second phase of fabricating the module 10. Additionally, the positive pressure transducers 35 and gates 36 are added during the second phase of fabricating the module 10.

After the module 10 is fabricated, tested and functioning as designed, the atom receiving unit 32 receives an atom or groups of atoms and/or a molecule or groups of molecules and feeds the atom(s) into the chemical reaction unit 33, where the atoms are combined via chemical reaction into the material, chemicals, or molecules required. The process is very similar to chemical vapor deposition (CVD) processes use in the semiconductor manufacturing arts, where one or more volatile precursors, which react and/or decompose on a substrate surface, are provided to produce the desired deposit. The atoms and/or molecules are received via a stream of atoms and/or molecules from the deposition cyclotron 83 fed by the atomic reservoir 84 and controlled by the master machine 100. The atoms and/or molecules in the stream should be no larger than the diameter of the beam channel emitted by the cyclotron; typically they should have a major dimension no larger than about 5 nanometers, about the same as the LASER (gamma) knife in current use. For further support, please refer to U.S. Pat. Nos. 8,067,741; 5,374,974; and 5,373,833, each of which is hereby incorporated herein, in its entirety, by reference thereto. After the atoms and/or molecules in the stream have been received in the atom receiving unit 32 in a quantity sufficient to carry out a chemical reaction in the procedure, the atoms and/or molecules are driven from the atom receiving unit 32 into the chemical reaction unit 33, by generating pressure via the pressure transducers 35 located in the atom receiving unit 32. FIG. 2B illustrates the gates 36 between the atom receiving unit and the chemical reaction unit 33 open to permit the delivery of the atoms and/or molecules into the chemical reaction unit 33. All other gates 36 are closed at this stage.

Figure 2C:
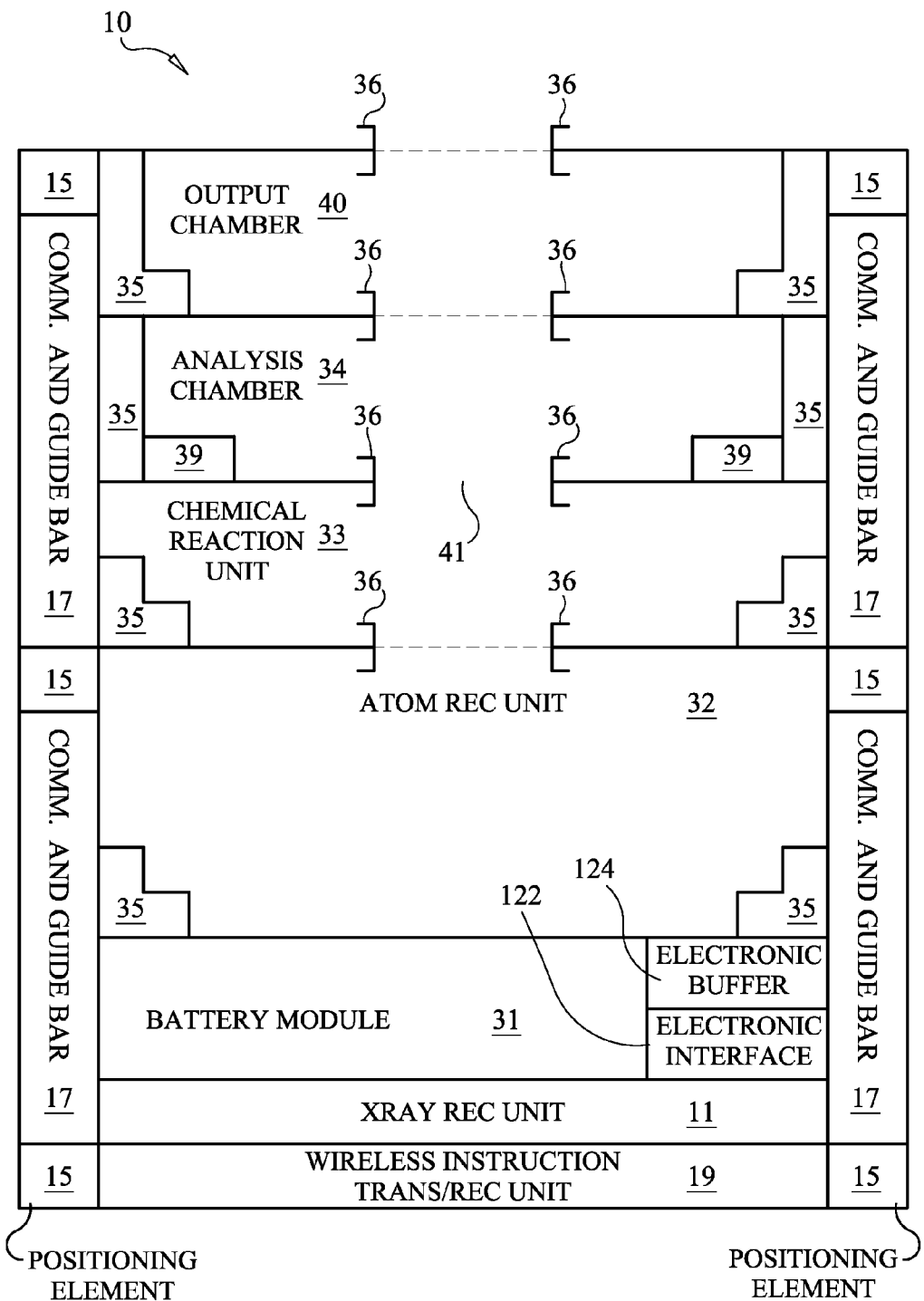
FIG. 2C is a schematic illustration of a module showing gates open between the chemical reaction unit and the analysis chamber, according to an embodiment of the present invention.

After the chemical reaction unit has completed a reaction to form a desired material, the material is released into the analysis chamber 34 by use of the pressure transducers 35 in the chemical reaction unit 33, which generate pressure within the chemical reaction unit 33 that serves as a driving force to drive the material into the relatively lower pressure analysis chamber 34. FIG. 2C illustrates the gates 36 between the chemical reaction unit 33 and analysis chamber 34 open to permit the delivery of the material into the analysis chamber 34. All other gates 36 are closed at this stage. The functioning of the pressure transducers is an automated procedure, like the other steps described herein, which operate according to the programming algorithms being run on the master machine 100. Chemical reaction technology is currently available as known to those of ordinary skill in the art.

Figure 2D:
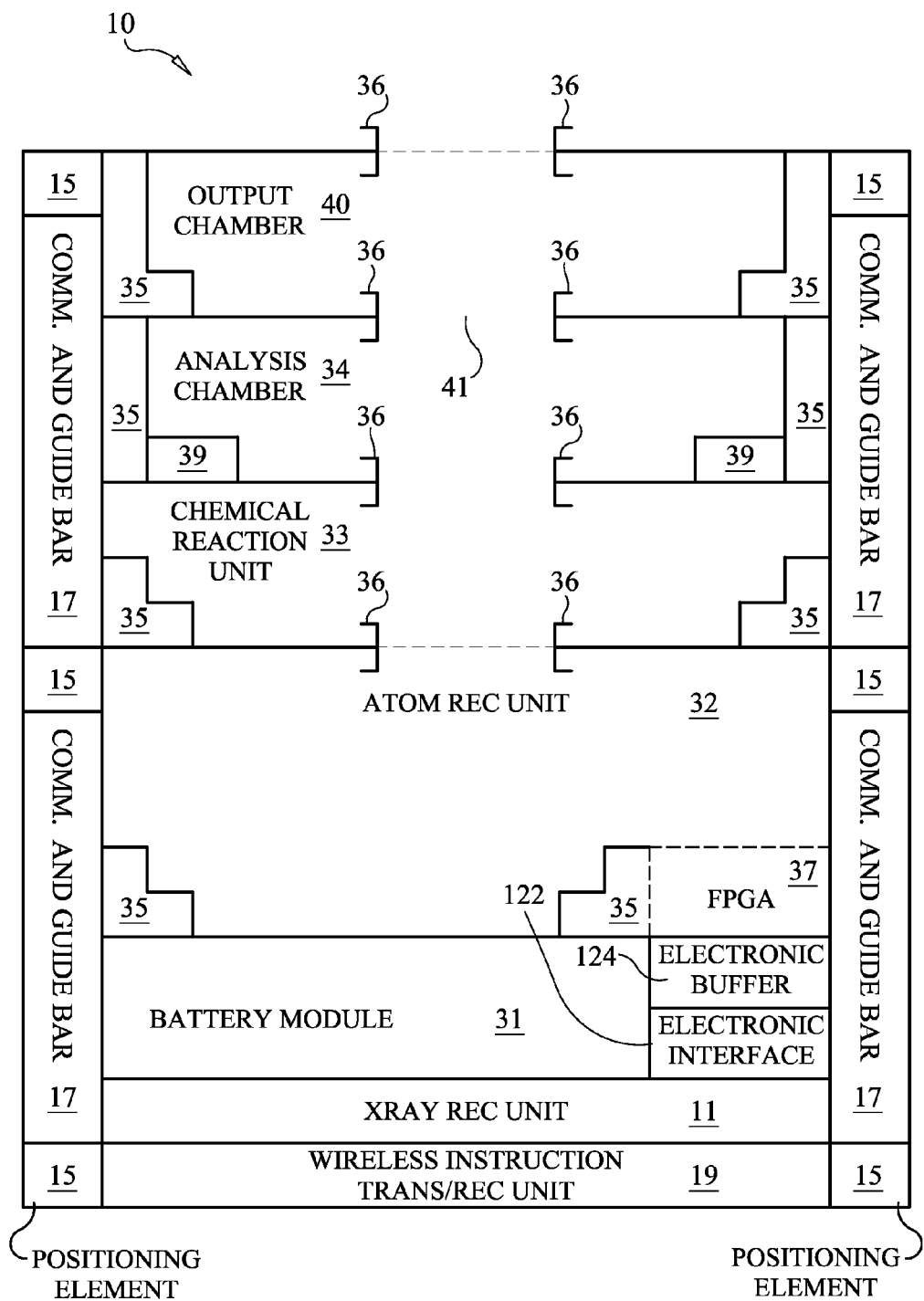
FIG. 2D is a schematic illustration of a module with gates open between the analysis chamber and the output chamber, according to an embodiment of the present invention.

The analysis chamber 34 contains chromatography unit 39 to facilitate the process of analyzing mixtures and substances. Chromatography is used to monitor the progress of a reaction, identify compounds present in a given mixture, and determine the purity of a substance. After the material within the analysis chamber 34 is analyzed, if determined to be correct as to the expected composition, the material is released to the output chamber 40 (FIG. 2D). Otherwise, encapsulation, removal or dissipation is carried out in a manner as described above. Release of the material is accomplished by use of the pressure transducers 35 in the analysis chamber 34, which are positive pressure transducers with the purpose of forcing the material, out of the chamber in the same manner as described above with regard to forcing material out of the chemical reaction unit 33. Release of the material, to the surgical target, from the output chamber 40, may be time released, as per algorithms programmed into the master computer 95. Wireless communication from element 86, within the master machine 100 controls the fabrication of the module 10, the testing of the module 10, activities of the module 10, movement of the module 10, and movement and release of the material/substance at all times.

After the second phase of fabricating the module 10 is finished, if it is determined the module 10 is non-functioning or that the material analyzed is incorrect; the module 10 is encapsulated in bio-compatible material to protect the human body from any harmful effects of the non-functioning module remaining within the human body indefinitely. Also, a non-functioning module 10 can be surgically removed if necessary if long term lingering within the tissue, cavity, and organ would be harmful to the body. In addition, as technology improves, forces outside of the body can dissolve the module within the human body if impairment results from leaving the module 10 within the body long term.

In time, after the technology has progressed, the number of phases of fabricating modules may be reduced to as few as only one phase of fabrication. FIGS. 2A, 2B, 2C, 2D, etc. are used to demonstrate one embodiment of a method of fabricating a module 10. A multitude of phases can be used. A multitude of types and shapes of modules can be fabricated.

In time, after the technology has advanced, field programmable gate arrays (FPGA) can be used in fabricating the highly developed, more complex modules, can be re-programmed to sophisticated capabilities without removing the module 10 from the body. That is, the field programmable gate arrays could allow: faster transmission, high bandwidth, faster atom downloading, etc. FIG. 2D illustrates optional inclusion of an FPGA 37. FPGA's could be used in a similar manner to the way in which they are used to recharge heart pacemakers, for example.

In time, after the technology has advanced, stem cells, that are biological cells found in all multicellular organisms, may be downloaded and developed, into new organisms such as new teeth, bone structure, and other types of body features/functions. The stem cells, biological cells are not indicated in any of the drawings.

FIG. 2C is a schematic illustration of module 10 with gates 36 open between the chemical reaction unit 33 and the analysis chamber 34, according to an embodiment of the present invention. The other gates between chambers 34 and 40, and between 40 and the surgical target location are closed, occupying the positions indicated by the dashed lines in FIG. 2C. The material is forced out of the chemical reaction 33 unit into the analysis chamber 34 by use of the pressure transducers 35.

FIG. 2D is a schematic illustrating the gates 36 open between the analysis chamber 34 and the output chamber 40, see the gateway space indicated by reference numeral 41. The other gates 36, i.e., between 33 and 34, and between 40 and the surgical target location outside of the module 10 and between chambers 32 and 33 are closed as indicated by the dashed lines. The material is forced out of the analysis chamber 34 into the output chamber 40 by use of the pressure transducers 35 in the analysis chamber 34.

Figure 2E:
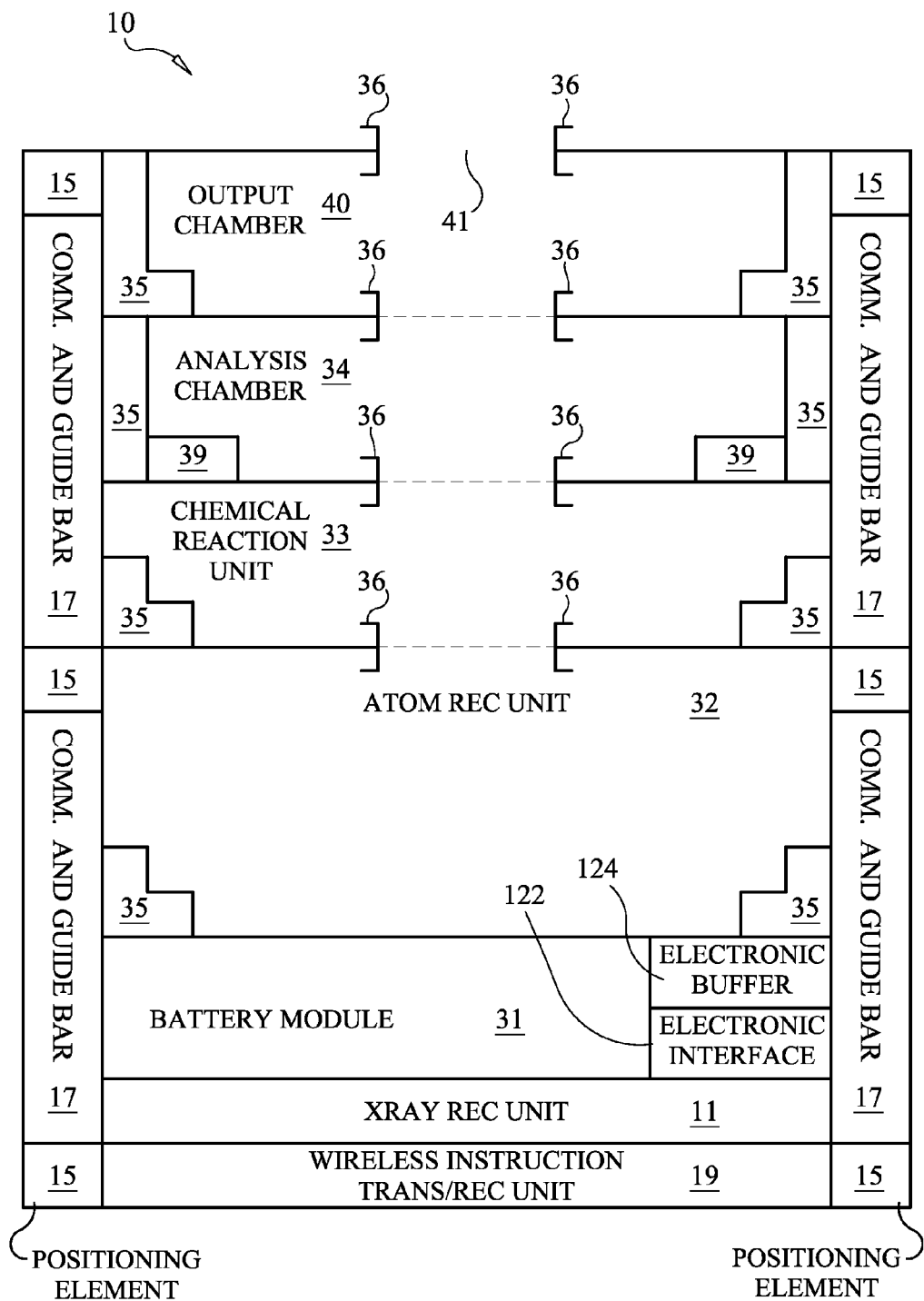
FIG. 2E is a schematic illustration of a module with gates open between the output chamber and the surgical target (i.e., outside the module), according to an embodiment of the present invention.

FIG. 2E is a schematic illustrating the gates 36 open between the output chamber 40 and the surgical target (i.e., outside the module 10), according to an embodiment of the present invention. The gates 36 between chambers 32 and 33, between 33 and 34 and between chambers 34 and 40 are closed as indicated by the dashed lines. The material is forced out of the output chamber 40 to the surgical target 43 by use of the pressure transducers 35 in the output chamber 40.

Figure 2F:
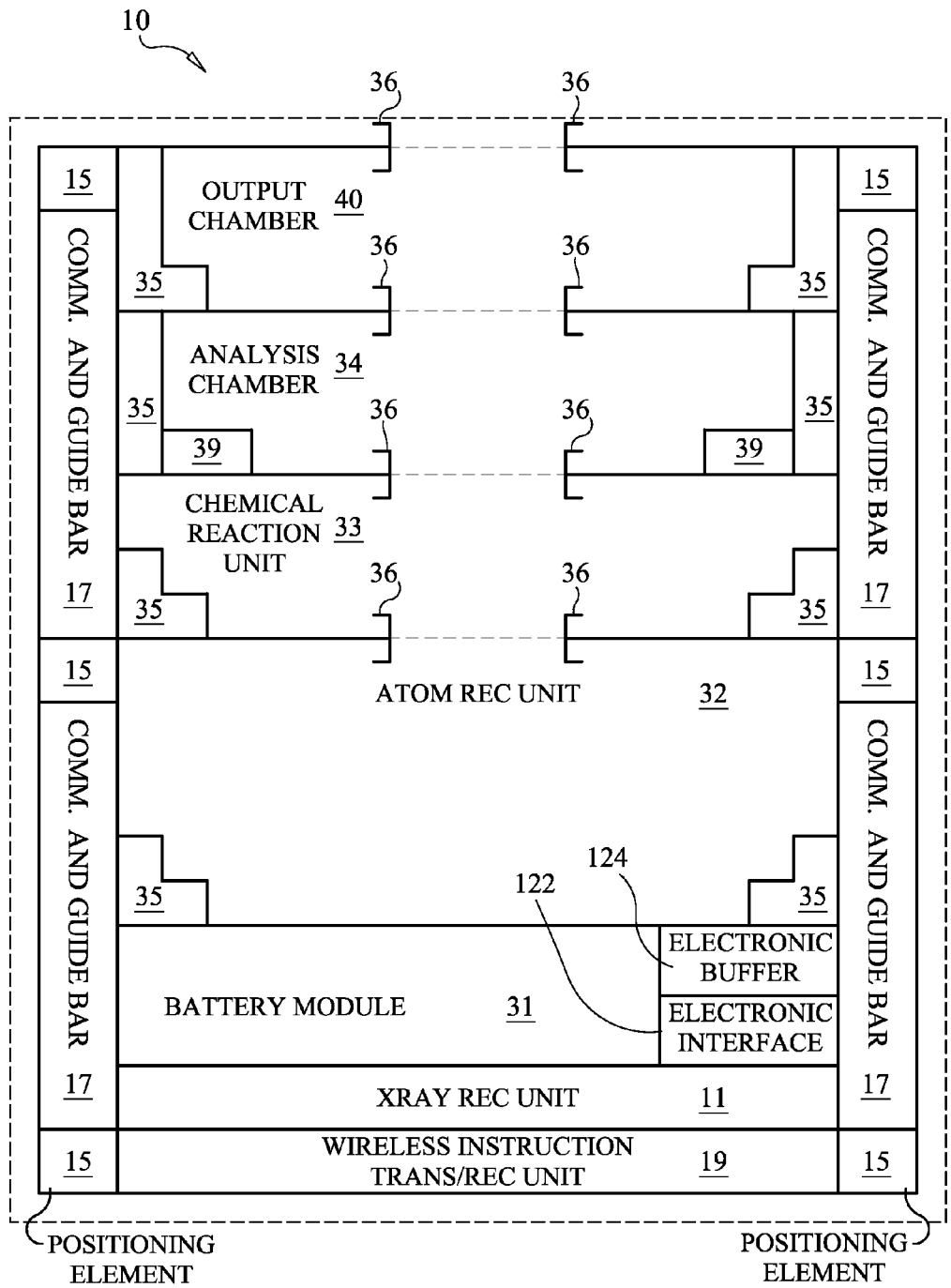
FIG. 2F is a schematic illustration showing encapsulation of the module after it has been determined to be non-functional, according to an embodiment of the present invention.

FIG. 2F is a schematic illustration showing encapsulation of the module 10 after it has been determined to be non-functional, according to an embodiment of the present invention. The module 10 is encapsulated with a bio-compatible material 42, which may be a material as described above. Alternatively, the encapsulation material may include properties of transient electronics that dissolve after a predetermined amount of time, such as magnesium oxide encapsulation layer and silk overcoat. An example of this is described in McCormick, "Disappearing Act: Biocompatible Electronics Vanish When No Longer Needed, Northwestern Engineering, Sep. 27, 2012, which is hereby incorporated herein, in its entirety, by reference thereto.

The encapsulating of the module causes no long term damage or harm to the tissue if left at this position indefinitely. The broken line 42 indicates the capsule surrounding the module 10. In addition, as technology improves, forces outside of the body can dissolve the module within the human body if leaving the module within in the body would result in impairment to the body if left indefinitely.

Figure 3A:
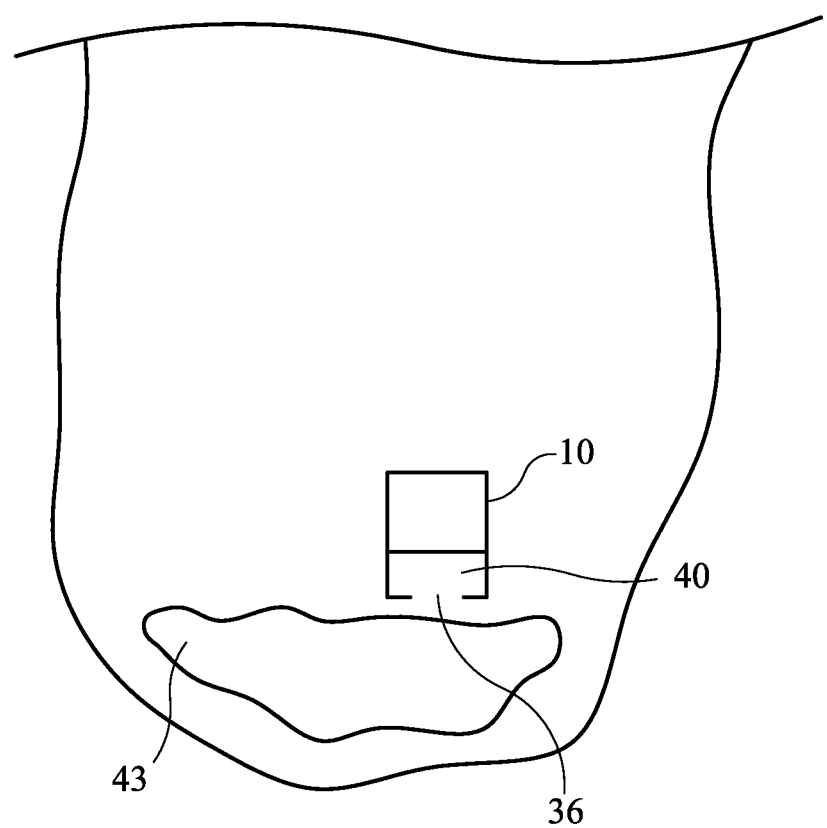
FIG. 3A is an illustration of a surgical target area in need of correcting, restoration and/or enhancement, and application of a module thereto, according to an embodiment of the present invention.

FIG. 3A is an illustration of a surgical target area 43, in this case, the brain in need of: correcting, restoration and/or enhancement. The module 10 is shown; the open gates 36 to the output chamber 40 are also indicated, according to an embodiment of the present invention.

Figure 3B:
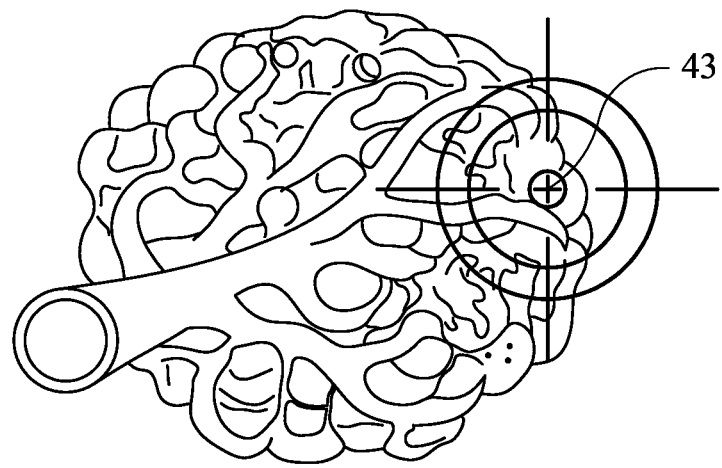
FIG. 3B is another illustration of a surgical target area in a brain in need of: correcting, restoration and/or enhancement.

FIG. 3B is another illustration of a surgical target area 43, in this case, the brain in need of: correcting, restoration and/or enhancement.

Figure 4:
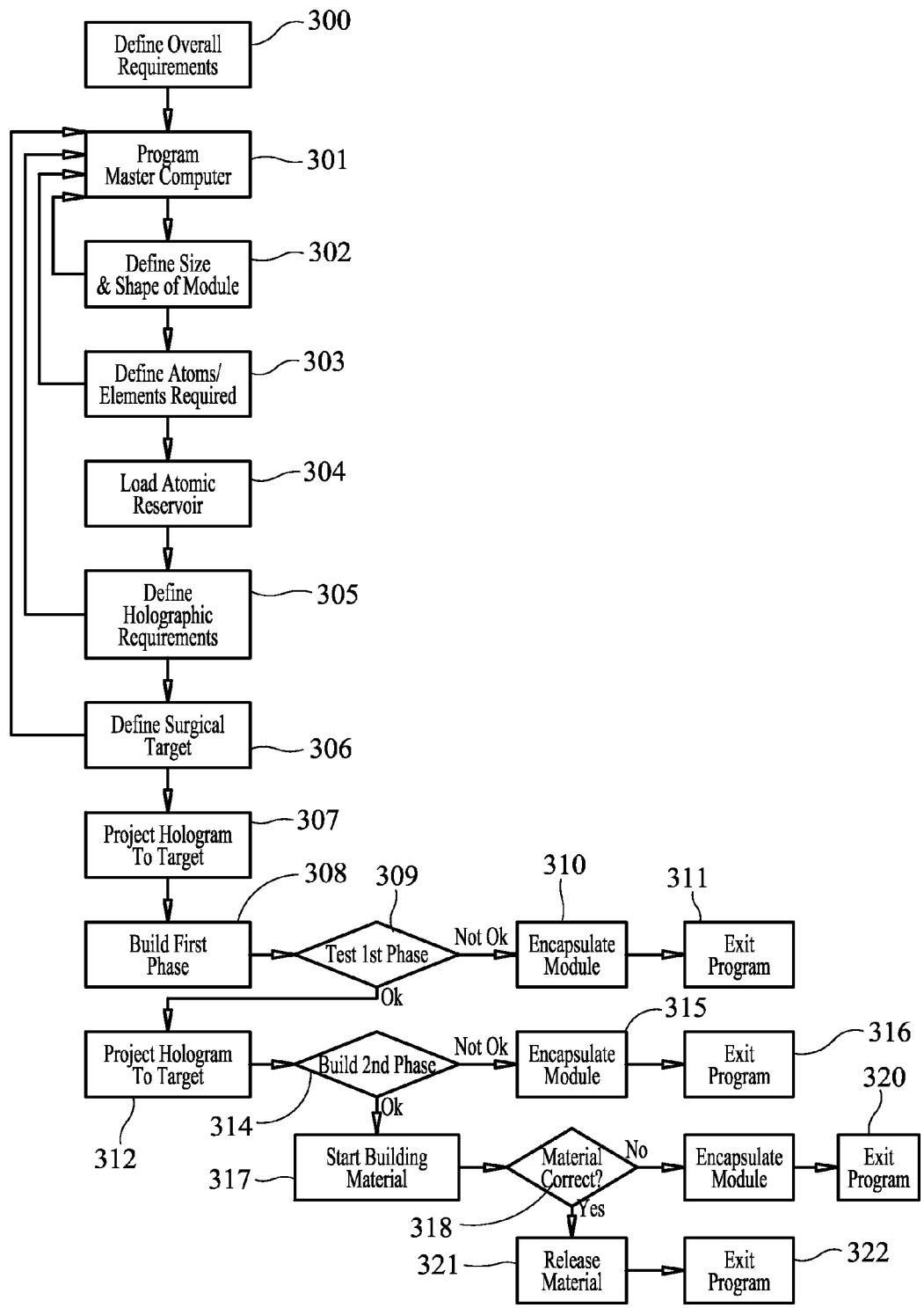
FIG. 4 is a flow chart illustrating events that may be carried out during a procedure according to an embodiment of the present invention.

FIG. 4 is a flow chart illustrating events that may be carried out during a procedure according to an embodiment of the present invention.

Description of the Events:

At event 300, the overall requirements of the project are defined. For example, the required dimension of the module(s) to be built, the elements/atoms/molecules required, and the types of biocompatible encapsulated material required are defined.

At event 301, the requirements are programmed into the master computer 95

At event 302, the size and shape of the module are defined and programmed into the master computer. Specifics including the location within the body are taken into consideration: for example a module to be fabricated in the brain may have dimensions of about 500 microns width×500 microns thickness×1000 microns length, and an example of a module fabricated in the lungs may have dimensions of about 5000 microns width×5000 microns thickness×1000 microns length.

At event 303, the atoms/elements/molecules/compounds are defined and programmed into the master computer, based upon the type of therapeutic and medicinal material required. The four most common elements in living organisms are carbon, hydrogen, oxygen and nitrogen, and will commonly be included in the atoms/elements/molecules defined. Other atoms/elements/molecules/compounds that may be defined here include, but are not limited to: L-Leucine, L-Isoleucine (BCAA), L-Valine (BCAA), L-Lysine, L-Threonine, L-Methionine, L-Phenylalanine, L-Tryptophan. Non-Essential Amino Acids: L-Arginine, L-Cystine, L-Alanine, L-Aspartic Acid, L-Glutamic, L-Glycine, L-Histidine, L-Proline, L-Serine, and/or L-Tyrosine.

At event 304, the required atoms/elements are loaded into the atomic reservoir 84. The reservoir 84 is loaded by attaching canisters or tanks, such as hydrogen oxygen, or nitrogen tank or canister to the atomic reservoir 84. The elements/atoms are released from the atomic reservoir to the deposition cyclotron as programmed by the master computer 95. The reservoir 84 is located external of the master machine 100, like the cyclotron 83.

At event 305, the three dimensional holographic requirements are defined and programmed into the master computer. As indicated above, the requirements may include, but are not necessarily limited to items such as: the location within the body, for instance, if a module was fabricated in the brain, it may be 500×500×2000 microns, the type of medicine used, type of atom/molecule, etc. A module fabricated in the lungs may be 5000×5000×1000 microns. In most cases the size of the module would be determined be the area (target location) of where the module is placed. Also, the amount of medicine, timeframe of the release of the medicine or therapeutic material required may be large, so as, a larger module must be fabricated.

At event 306, the parameters and location of the surgical target are defined and programmed into the master computer 95. The location of the surgical target is defined by the position of the module 10 relative to the location of the area in the body that it is to be placed (surgical target), whereas the medicine, medicinal material must be released to the surgical target. The surgical target can be defined by using triangulate angles relative to reference points in the body.

At event 307, the hologram of the first phase fabrication of the module is projected to the target location. The hologram is targeted to the location required, can use reference points for properly locating the hologram, such as, five microns from point A, ten microns of point B, ten microns from point C. This is a similar concept to surveying an area of land, using three points, to mark a certain location, but in three dimensions.

At event 308, the first phase of fabricating the module 10, atom-by-atom (preferably, but may be molecule-by-molecule or compound-by compound, or combinations of these, etc.), is performed and completed.

At event 309, the module 10, as it exists after completion of the first phase, is tested. Specifically, after the first phase, the wireless instruction transmitting/receiving unit, X-ray receiving unit, electronic interface, electronic buffer, and the module battery are tested. If functioning correctly, the wireless instruction trans/receiving unit sends a signal indicating the first phase fabrication to this point is correct and the module is functioning correctly. When the results of testing module 10 at event 309 determine that the module 10, is non-functional, event 310 is carried out.

At event 310, the module 10 is encapsulated and left at the surgical target area.

At event 311, the program exits.

When the results of testing module 10 at event 309 determine that the module 10, is functional, event 312 is carried out.

At event 312, after the first phase is tested OK, the second phase hologram is projected to the surgical target area. The first phase of fabricating the module is building the module as indicated on FIG. 2A. The elements fabricated during this phase are: Communication and guide bar 17, positioning elements 15 (physical elements), wireless instruction rec/trans unit 19, electronic interface 122, electronic buffer 124 and the module battery 31. The phases differ by the different types of elements/units fabricated during the dissimilar phases. With more complex modules, three or four phases of fabrication may be required. The holograms are preset (programmed into the master computer 95) and projected to within the body after each of the phases has been tested and is functioning correctly.

At event 314, the second phase of fabricating the module 10, atom-by-atom (and/or molecule-by-molecule and/or compound-by-compound, etc.) is carried out and completed, and the module 10, as it exists at the completion of the second phase processing, is tested. When test results from event 314 indicate that the second phase module 10 is non-functional, processing proceeds to event 315.

At event 315, the module 10 is encapsulated and left at the surgical target area.

At event 316, the program exits.

When test results from event 314 indicate that the second phase module 10 is functional, processing proceeds to event 317. At event 317, after the second phase fabrication is tested OK and thus the module 10 is functioning correctly, the production of the treatment material (medicinal substance or therapeutic material) required is carried out in the chemical reaction unit 33. The process indicated at event 317 starts with the atoms/molecules being downloaded into the atom receiving unit 32, and then they are sent to the chemical reaction unit 33 and combined into the treatment material required for the procedure. Again, the algorithm programmed into the master computer 95 executes this process out step-by-step until the treatment material is intact.

At event 318, the material or substance produced during event 317 for treating a medical condition is analyzed by the chromatography unit 39 within the analysis chamber 34 of module 10.

If the analysis results of event 318 indicate that the material does not have the intended chemical composition, processing proceeds to event 319 and the module 10 is encapsulated at event 319 and left at the surgical target area.

At event 320, the program exits.

If the analysis results of event 318 indicate that the material does have the intended chemical composition, processing proceeds to event 321. At event 321 the module 10 releases the material to the target area as per the algorithm programmed into the master computer.

At event 322, the program exits.

FIG. 5 is a schematic illustration of hardware components included in system 100 according to an embodiment of the present invention. The components include: the MRI/CT section 90, the three dimensional holographic projector 85, NMR section 80, the wireless instruction transmitter/receiver 86, X-ray generator 81, and X-ray transmitter 82. Also included in FIG. 5: the atomic reservoir 84 and the cyclotron/deposition technology section 83.

FIG. 6 is a block diagram of a computer system that may be implemented in system 100 according to an embodiment of the present invention. This figure represents a typical computer system, components of which, or all of which may be employed in system 100. The computer system 700 includes any number of processors 702 (also referred to as central processing units, or CPUs, and, for example, which may be employed in the computer controller 95 of system 100, as well as one or more sub-sections described) that are coupled to storage devices including primary storage 706 (typically a random access memory, or RAM), primary storage 704 (typically a read only memory, or ROM). As is well known in the art, primary storage 704 acts to transfer data and instructions unit-directionally to the CPU and primary storage 706 is used typically to transfer data and instructions in a bi-directional manner. Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers, any of which may be included in console 95, for example. Interface 710 may include interfaces to NMR 80 and CT/MRI 90 sections, and sections illustrated in FIG. 5. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

Figure 7:
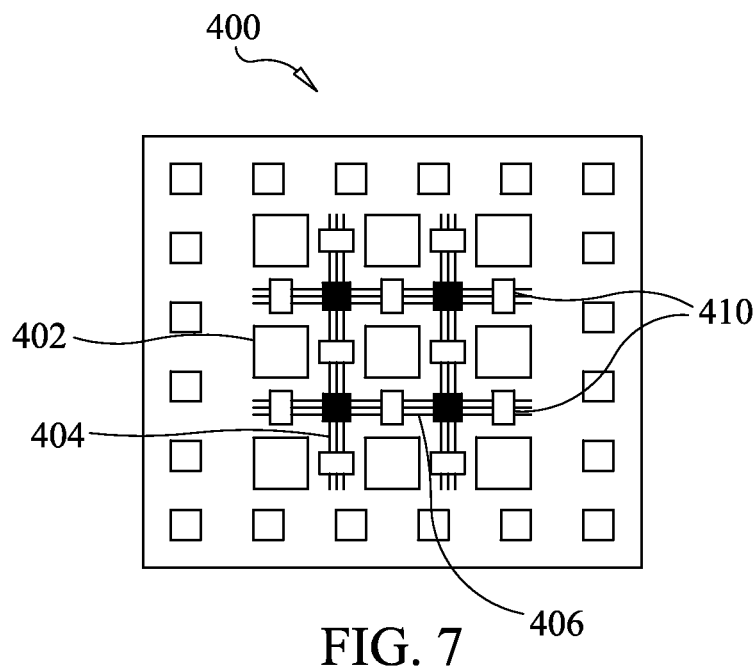
FIG. 7 schematically illustrates architecture of an FPGA that can be used in a module according to an embodiment of the present invention.
Figure 8:
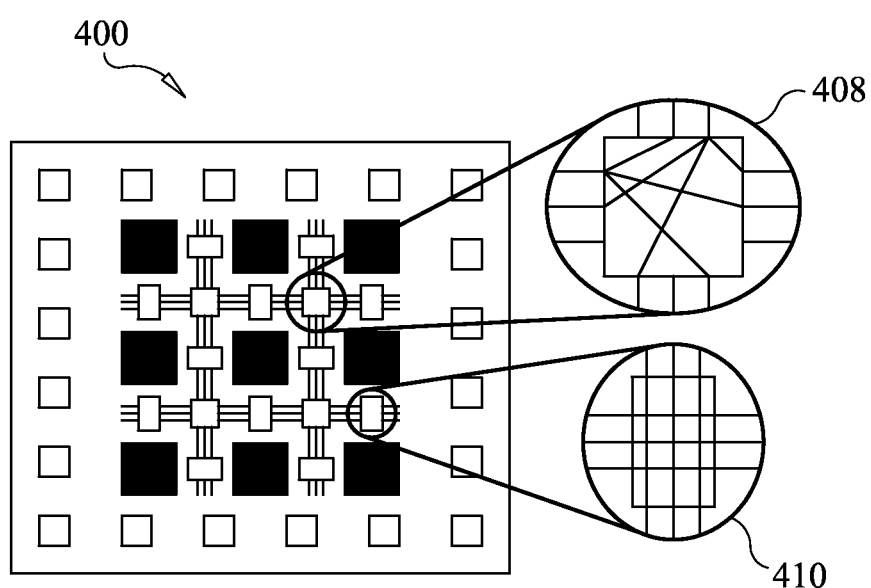
FIG. 8 is another schematic illustration of the FPGA of FIG. 7, showing enlarged views of a switchbox and a connection box.

FIG. 7 schematically illustrates architecture of an FPGA 400 that can be used in a module 10 according to an embodiment of the present invention. The FPGA 400 architecture comprise an array of logic gates making up configurable logic blocks 402 interconnected by vertical 404 and horizontal 406 wiring channels. The FPGA 400 typically includes one or more lookup tables, registers and multipliers/multiply accumulate units (MAC). Programmable switches 408 and connection boxes 410 (see also FIG. 8) interconnect the logic blocks 402 and provide the ability to program the FPGA 400 to perform various different functions.

Figure 9:
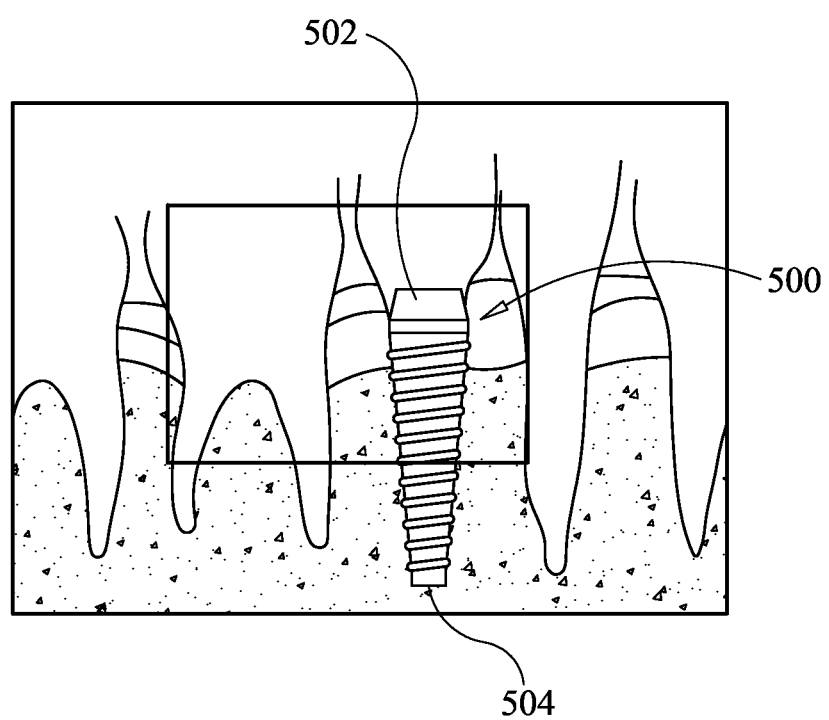
FIG. 9 illustrates a dental implant including a crown and post having been implanted and fabricated atom-by-atom.

FIG. 9 illustrates a dental implant 500 including a crown 502 and post 504 having been implanted and fabricated atom-by-atom.

The present invention provides embodiments that overcome shortcomings of the prior art by using multiple advanced technologies, including semiconductor-manufacturing methodology, nano-manufacturing techniques, and integrating these techniques, to produce a bio-compatible module. The module will then be transformed into a multifunctional, enhanced, multipurpose module. After implanting the module into a patient's body, the invention allows communication to the module and subsequently developed modules: in addition, positioning and guiding the module within an organ, body sub-system or surgical target is provided by means of a Nuclear Magnetic Resonance (NMR) control system if it becomes necessary to move or re-position the module. Accordingly, the invention provides for the detection, control and positioning of a module within the organ, body sub-system or cavity.

The module(s) is/are then expanded, enhanced and enlarged to the required proportions to receive atoms and groups of atoms that are assembled into material (medicines and/or other material) to correct or enhance the physiological deficiencies or embellish conditions of the human body.

Once expanded, the module will be transformed into a receiving module large enough to be a reformation receiving module that can provide medicine, material, whatever substance is required to correct the physiological deficiency or enhance circumstances of the targeted organ, tissue or area in need of restoration or enhancement.

The module 10 is produced, using a three dimensional holographic blueprint projected to the surgical target, allowing for computer-assisted surgery of the procedure within the cavity, body sub-system, vessel or organ to be surgically targeted.

The invention will utilize a three dimensional holographic blueprint, to fabricate a module, which is projected to the surgical target from outside of the body by three dimensional holographic technology. The prearranged surgical target will be programmed into a master computer with respect to the size, shape and location of the module within the human body.

The invention will utilize three dimensional holographic generators, projecting an image beam, from an image projection mechanism within a master machine to display an image, wherein: the three dimensional holographic target module is a plurality of overlay holograms. The invention will utilize an illumination system comprises multiple light emitting devices which emit light beams having a predetermined wavelength and a three dimensional holographic optical element directed towards a predetermined surgical target.

The invention will make use of a collection of subholograms which together correspond to a three dimensional holographic image will be produced to construct add on features and enhancements to the module. This allows for additional sub-units to be fabricated after an initial module is fabricated.

Various essentials of the present invention include one or more of manufacturing of the module/s, the detection of the module, guiding and controlling, positioning and using the module to clear human vessels by means of a Nuclear Magnetic Resonance (NMR) control system. Within the scope of at least one embodiment of the present invention, a module is produced, allowing for computer-assisted fabrication of the module of the procedure within the cavity, body sub-system or organ, within the human body to be surgically targeted. The module and subsequent multifunctional and multipurpose modules will be controlled and guided by a method described by Zurn in U.S. patent application Ser. No. 11/895,681, filed on Aug. 27, 2007, now U.S. Pat. No. 7,979,108, both of which are hereby incorporated herein, in their entireties, by reference thereto.

Within the scope of at least one embodiment of the present invention, a module is produced, using a three dimensional holographic blueprint projected to the surgical target, allowing for computer-assisted fabrication of the module within the cavity, body sub-system, vessel or organ, within the human body to be surgically targeted. The module and subsequent enhanced, multipurpose modules can be constructed into a vessel clearing apparatus by a method described by Zurn in U.S. patent application Ser. No. 13/356,884, filed on Jan. 24, 2012, which is hereby incorporated herein, in its entirety, by reference thereto.

Within the scope of at least one embodiment of the present invention, a module is produced, within the human body, using a three dimensional holographic blueprint projected to the surgical target, allowing for computer-assisted fabrication of the module within the cavity, body sub-system, vessel or organ to be surgically targeted. The module and subsequent enhanced, multipurpose modules can be constructed into an analysis and clearing module, within the human body, by a method described by Zurn in U.S. patent application Ser. No. 13/569,204 filed on Aug. 8, 2012, which is hereby incorporated herein, in its entirety, by reference thereto.

The invention provides a method of creating holograms, comprising: creating at least one hologram in a first subdivision of a three dimensional holographic module having predetermined proportions; creating at least one hologram in a second subdivision of predetermined three dimensional holographic proportions, the second subdivision being adjacent to the first subdivision.

A module such as described according to a description of the present invention can be used in many medical applications. As mentioned, it may be employed in miscellaneous types of body sub-systems, organs, and cavities within the human body. The invention can be used to sustain and to eliminate pathological body sub-system deficiencies.

The module can be fabricated into a heart pacemaker, fabricated within the body, by use of outside forces, without the need for breaching the body. The battery of the heart pacemaker could be re-charged, without the need, for breaching of the body.

According to a described description of the invention, a biocompatible MEMS module and subsequent multipurpose, multifunctional modules are assembled, including: a communication element configured to receive radio frequency energy from a source external of the device; radio frequency receiving unit; a communication link between the communication element and each of the MEMS device regions.

The invention will fabricate a module, constructed using nanotechnology, to create a microelectromechanical device (MEMS). Each module may have different dimensions, such as dimensions of (100×100×50 microns): smaller modules will be used for smaller targeted areas of the sub-systems of the body. The size of the module is determined, at least in part, by the size of the organ, duct, vessel, body sub-system, tissue or cavity in need of the analysis and of the procedure required.

The module will include wireless instruction transmit and receive units, allowing for communication between the module and the master machine outside of the human body.

The module will also include an X-ray receiving unit and X-ray energy conversion unit. The X-ray energy will be converted to electrical energy used to power the module.

Also fabricated within the module are guide bars, these guide bars include communication circuits (bus) connecting to all sections within the module. Further included within the module, are positioning elements, used for the placement of the three dimensional holographic blueprint, to fabricate a module, which is projected to the surgical target from outside of the body by three dimensional holographic technology.

The module also includes the following sections: the atomic receiving unit and the chemical reaction unit. After fabricating the module atom-by-atom, three categories of channels are sent to module from master machine: one category, wireless instruction signals are sent to the wireless receiving to guide and control the activities and movement of the module. In addition, a second category, X-ray energy is sent to the X-ray receiving section, which is converted into electrical energy to power the battery in the module. The master machine's chemical vapor deposition/cyclotron technology device sends the stream of atoms, which comprises the third category. The stream of atoms is sent to the atomic receiving unit within the module.

The wireless instructions are received by the wireless instruction transmit/receiving unit and are then transmittable via the communication links (paths) within the communication links to other module sub-sections within the module. The guide and control wireless instructions are in the form of information packets. The X-ray energy is converted into electrical energy to power the batteries in the module. The stream of atoms is assembled within the module into the required material: chemicals and molecules.

The module receives three types of non-destructive energy: X-ray and wireless instructions (e.g., in the form of RF energy) and a stream of atoms or groups of atoms. The X-ray energy is converted to electrical energy. The wireless instructions are used for guiding and controlling and activities of the module, plus, controlling the stream of atoms. The non-destructive energy is supplied to the module from a source outside of the patient's body, e.g., from a NMR machine or other controller. The X-rays are within a voltage range of about 12 to about 120 keV (0.10 to 0.01 nm wavelength), and are applied in short duration not harmful to the human body. The wireless instructions are provided as RF energy conforming to IEE 802.11 standards used in implementing wireless local area network (WLAN) computer communications in the 2.4, 3.6 and 5 GHz frequency bands. The stream of atoms is assembled within the module into the required chemicals and molecules by use of the wireless instructions.

Coded wireless instructions (guide and control signals) are sent to the module to guide and control the activities within the module. The instructions are sent from an instruction transmit/receiving unit outside the patient's body to an instruction transmit/receiving unit of the module inside the patient's body. Instructions are sent within a packet string in either direction. The method of delivery of the instructions is similar to the Internet Protocol packet. The packet contains header, body and trailer information that is decoded by the MEMS module for controlling functions of the module. The instructions are sent from a down link transmission unit 86, received, then decoded within the clearing module and processed. The instructions are executed by the module to guide and control the module to perform the necessary procedures.

The data transmission from a MEMS module, referred to as an uplink transmission, transmits to a master NMR information that is necessary for fine tuning adjustments with respect to the activities of the module. This allows for "real time" feedback to control the activities within the MEMS module. Data transmission from the NMR, referred to as a downlink transmission, transmit information to the MEMS module necessary for controlling function of the module. This data from the NMR may adjust sensing activities and guide activities of the MEMS module such as if the module must be slightly moved within the body. After fabricating the module, slight adjustment of the movement, of the module may transpire.

Nuclear Magnetic Resonance (NMR) techniques are used for possible positioning and guiding the module during a procedure on a patient. Precise movement of the module is critical to avoid damaging an organ, cavity body sub-system or any other human tissue that is not intended to be destroyed or removed during the procedure.

The module is fabricated of material tolerated by the human body, and can be applied within organ, body sub-systems, tubes, cavities, blood vessels and/or human tissue in the body of a living animal, a living human or some other intricate accessible place within either. Modules can comprise a resilient flexible substance substantially inert to bodily fluids (e.g., silicone, or other biocompatible polymer having similar properties). By means of the positioning elements, the NMR system can directly determine and track the location of the module at all times.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A module for use inside a living body, said module comprising:
   an instructions receiver configured to receive wireless transmissions of instructions from a master controller located outside of the body when said module is inside the body;
   an energy receiver configured to receive wireless transmission of non-destructive energy from the master controller located outside of the body when said module is inside the body;
   a battery;
   an electronic interface configured to convert the non-destructive energy from the energy receiver to electric energy to power the module;
   a communications and guide element electrically connected to said instructions receiver, said energy receiver and said battery;
   an atom receiving unit;
   a chemical reaction unit that receives atoms, atoms and molecules, molecules, molecules and compounds, or compounds from said atom receiving unit and carries out a reaction of said atoms, atoms and molecules, molecules, molecules and compounds, or compounds in the presence of a catalyst to produce a treatment material;
   an analysis chamber in fluid communication with said chemical reaction unit, said analysis chamber comprising a unit to receive said treatment material from said chemical reaction unit and chemically analyze said treatment material to determine whether the treatment material is a correct or expected composition; and
   encapsulation material;
   wherein at least one of said instructions receiver, energy receiver, battery, and communications and guide element comprises a microelectromechanical system (MEMS);
   wherein said module is configured and dimensioned to be moved within the living body in response to signals sent from the master controller located outside of the body; and
   wherein said encapsulation material is applied to prevent application of said treatment material in the living body, when it is determined that the treatment material is not the correct or expected composition.

2. The module of claim 1, further comprising at least one positioning element configured to be tracked by the master controller, so that the master controller can identify location and orientation of said module.

3. The module of claim 1, wherein said electronic interface is configured to convert said non-destructive energy to said electric energy to charge said battery.

4. The module of claim 1, wherein said unit to receive said treatment material from said chemical reaction unit and chemically analyze said treatment material comprises a chromatography unit configured to chemically analyze said treatment material by chromatography.

5. The module of claim 1, further comprising an output chamber in fluid communication with said analysis chamber, said output chamber having at least one gate openable to place said output chamber in fluid communication with a location external of said module and closable to close off fluid communication with the location external of said module, wherein after said treatment material within said analysis chamber is analyzed and determined to be acceptable, said output chamber receives said treatment material from said analysis chamber.

6. The module of claim 5, wherein said output chamber is configured to close off fluid communication with said analysis chamber after receiving said treatment material, and expel said treatment material to the location outside the module after opening said at least one gate.

7. The module of claim 1, further comprising a field programmable gate array (FPGA) configured to be reprogrammable to change functions of said module, wherein said reprogramming is performable from a location outside of the body while said module is inside the body.

8. The module of claim 5, further comprising:
   at least one gate interposed between said output chamber and said analysis chamber; and
   at least one gate interposed between said analysis chamber and said chemical reaction unit;
   wherein each of said gates is configured to open to allow fluid communication between the respective chambers and/or units that it is interposed, and wherein each of said gates is further configured to close to prevent fluid communication between the respective chambers and/or units that it is interposed.

9. The module of claim 5, further comprising at least one pressure transducer located in each of said chemical reaction unit, analysis chamber and output chamber.

10. A module for use inside a living body, said module comprising: an instructions receiver configured to receive wireless transmissions of instructions from a master controller located outside of the body when said module is inside the body;
   an energy receiver configured to receive wireless transmission of non-destructive energy from the master controller located outside of the body when said module is inside the body;
   an electronic interface configured to receive said non-destructive energy from said energy receiver and convert said non-destructive energy to electrical energy;
   a battery configured to receive the electrical energy converted by said electronic interface;
   at least one communications and guide element electrically connected to said instructions receiver, said energy receiver, said electronic interface and said battery;
   a chemical reaction unit configured to receive atoms, atoms and molecules, molecules, molecules and compounds, or compounds and carry out a reaction of said atoms, atoms and molecules, molecules, molecules and compounds, or compounds to produce a treatment material, wherein said atoms, atoms and molecules, molecules and compounds or compounds are combined in a chemical reaction to produce said treatment material;

an analysis chamber in fluid communication with said chemical reaction unit, said analysis chamber configured to receive said treatment material from said chemical reaction unit and chemically analyze said treatment material to determine whether the treatment material is a correct or expected composition;

wherein at least one of said instructions receiver, energy receiver, battery, and communications and guide element comprises a microelectromechanical system (MEMS);

wherein said module is configured and dimensioned to be moved within the living body in response to signals sent from the master controller located outside of the body; and wherein said module is encapsulated to prevent application of said treatment material in the living body, when it is determined that the treatment material is not the correct or expected composition.

11. The module of claim 10, wherein said non-destructive energy is X-ray energy and said electronic interface converts said X-ray energy to electrical energy.

12. The module of claim 10, further comprising an electronic buffer electrically connected between said electronic interface and said battery.

13. The module of claim 10, wherein said analysis chamber comprises a chromatography unit configured to chemically analyze said treatment material by chromatography.

14. The module of claim 10, further comprising an output chamber in fluid communication with said analysis chamber, said output chamber having at least one gate openable to place said output chamber in fluid communication with a location external of said module and closable to close off fluid communication with the location external of said module, wherein after said treatment material within said analysis chamber is analyzed and determined to be acceptable, said output chamber receives said treatment material from said analysis chamber.

15. The module of claim 14, wherein said output chamber is configured to close off fluid communication with said analysis chamber after receiving said treatment material, and expel said treatment material to the location outside the module after opening said at least one gate.

16. The module of claim 1, wherein said non-destructive energy is X-ray energy.

17. A module for use inside a living body, said module comprising:

an instructions receiver configured to receive wireless transmissions of instructions from a master controller located outside of the body when said module is inside the body;

an energy receiver configured to receive wireless transmission of non-destructive energy from the master controller located outside of the body when said module is inside the body;

an electronic interface configured to receive said non-destructive energy from said energy receiver and convert said non-destructive energy to electrical energy;

at least one communications and guide element electrically connected to said instructions receiver, said energy receiver and said electronic interface;

a chemical reaction unit configured to receive atoms, atoms and molecules, molecules, molecules and compounds, or compounds and carry out a reaction of said atoms, atoms and molecules, molecules, molecules and compounds, or compounds to produce a treatment material, wherein said atoms, atoms and molecules, molecules and compounds or compounds are combined in a chemical reaction to produce said treatment material;

an analysis chamber in fluid communication with said chemical reaction unit, said analysis chamber configured to receive said treatment material from said chemical reaction unit and chemically analyze said treatment material to determine whether the treatment material is a correct or expected composition;

wherein said module is configured and dimensioned to be moved within the living body in response to signals sent from the master controller located outside of the body; and wherein said module is encapsulated to prevent application of said treatment material in the living body, when it is determined that the treatment material is not the correct or expected composition.

18. The module of claim 17, wherein said non-destructive energy is X-ray energy.

* * * * *

UNITED STATES PATENT AND TRADEMARK OFFICE
CERTIFICATE OF CORRECTION

PATENT NO. : 9,962,533 B2  
APPLICATION NO. : 13/767671  
DATED : May 8, 2018  
INVENTOR(S) : Zurn Page 1 of 1

It is certified that error appears in the above-identified patent and that said Letters Patent is hereby corrected as shown below:

In the Specification

Column 2, Line 12, please delete "arrive a location" and insert --arrive at a location--.
Column 2, Line 65, please delete "a at least one".
Column 2, Line 66, please delete "embodiment,".

Signed and Sealed this  
Twenty-fifth Day of September, 2018

Andrei Iancu  
*Director of the United States Patent and Trademark Office*